(12) United States Patent
Ofek et al.

(10) Patent No.: US 9,700,224 B2
(45) Date of Patent: Jul. 11, 2017

(54) ELECTRICALLY CONDUCTIVE PATHWAY IN A CLOSED-ENDED CATHETER

(71) Applicant: C. R. Bard, Inc., Murray Hill, NJ (US)

(72) Inventors: Gidon Ofek, Salt Lake City, UT (US); Jason R. Stats, Layton, UT (US)

(73) Assignee: C. R. Bard, Inc., Murray Hill, NJ (US)

(*) Notice: Subject to any disclaimer, the term of this patent is extended or adjusted under 35 U.S.C. 154(b) by 200 days.

(21) Appl. No.: 14/657,157

(22) Filed: Mar. 13, 2015

(65) Prior Publication Data

US 2015/0182168 A1 Jul. 2, 2015

Related U.S. Application Data

(63) Continuation-in-part of application No. 14/209,600, filed on Mar. 14, 2013, now Pat. No. 9,456,760.
(Continued)

(51) Int. Cl.
*A61B 5/042* (2006.01)
*A61B 5/00* (2006.01)
(Continued)

(52) U.S. Cl.
CPC ............ *A61B 5/042* (2013.01); *A61B 5/6852* (2013.01); *A61L 29/06* (2013.01); *A61L 29/14* (2013.01);
(Continued)

(58) Field of Classification Search
CPC .................. A61B 5/042; A61B 18/1492
See application file for complete search history.

(56) References Cited

U.S. PATENT DOCUMENTS

| 3,416,533 A | 12/1968 | Fisher et al. |
| 3,769,984 A | 11/1973 | Muench |

(Continued)

FOREIGN PATENT DOCUMENTS

| CN | 201356648 Y | 12/2009 |
| WO | 92/17150 A1 | 10/1992 |

(Continued)

OTHER PUBLICATIONS

PCT/US14/26149 filed Mar. 13, 2014 International Search Report and Written Opinion dated Jul. 28, 2014.
(Continued)

*Primary Examiner* — Lee S Cohen
(74) *Attorney, Agent, or Firm* — Rutan & Tucker, LLP

(57) ABSTRACT

A closed-ended catheter assembly that includes an electrically conductive pathway is disclosed. The conductive pathway enables electrical ECG signals from a patient's heart to pass through the closed-ended tip of the indwelling catheter while still preventing unintended fluid flow. In one embodiment, a catheter assembly is disclosed and comprises an elongate catheter tube including a closed distal end. The catheter tube defines a lumen and includes a valve defined in the catheter tube to selectively enable fluids to pass therethrough. The catheter tube includes a conductive element that provides an electrically conductive pathway between the lumen and an exterior portion of the catheter. The conductive element includes an electrically conductive sleeve disposed within the lumen and is positioned proximate a hole defined in a catheter tube wall. The hole enables fluids in a vessel of the patient body in which the catheter tube is disposed to contact the sleeve.

7 Claims, 28 Drawing Sheets

Related U.S. Application Data

(60) Provisional application No. 62/013,494, filed on Jun. 17, 2014, provisional application No. 61/784,625, filed on Mar. 14, 2013, provisional application No. 61/952,813, filed on Mar. 13, 2014.

(51) Int. Cl.
*A61L 29/06* (2006.01)
*A61L 29/14* (2006.01)
*A61M 39/20* (2006.01)

(52) U.S. Cl.
CPC ..... *A61L 29/146* (2013.01); *A61B 2562/0209* (2013.01); *A61M 39/20* (2013.01)

(56) References Cited

U.S. PATENT DOCUMENTS

| | | | |
|---|---|---|---|
| 4,329,993 | A | 5/1982 | Lieber et al. |
| 4,592,372 | A | 6/1986 | Beranek |
| 5,005,587 | A | 4/1991 | Scott |
| 5,281,218 | A | 1/1994 | Imran |
| 5,348,554 | A | 9/1994 | Imran et al. |
| 5,383,922 | A | 1/1995 | Zipes et al. |
| 5,433,742 | A | 7/1995 | Willis |
| 5,531,679 | A | 7/1996 | Schulman et al. |
| 5,643,197 | A | 7/1997 | Brucker et al. |
| 5,772,642 | A | 6/1998 | Ciamacco, Jr. et al. |
| 5,888,577 | A | 3/1999 | Griffin, III et al. |
| 5,913,856 | A | 6/1999 | Chia et al. |
| 6,017,338 | A | 1/2000 | Brucker et al. |
| 6,032,061 | A | 2/2000 | Koblish |
| 6,440,488 | B2 | 8/2002 | Griffin, III et al. |
| 6,475,184 | B1 | 11/2002 | Wang et al. |
| 6,562,021 | B1 | 5/2003 | Derbin et al. |
| 6,912,423 | B2 | 6/2005 | Ley et al. |
| 7,231,259 | B2 | 6/2007 | Jenney et al. |
| 7,559,137 | B2 | 7/2009 | Beer et al. |
| 7,629,015 | B2 | 12/2009 | Anderson et al. |
| 7,766,907 | B2 | 8/2010 | Dando et al. |
| 8,075,969 | B2 | 12/2011 | Anderson et al. |
| 8,147,486 | B2 | 4/2012 | Honour et al. |
| 8,442,653 | B2 | 5/2013 | Gill |
| 8,543,222 | B1 | 9/2013 | Sochor |
| 8,620,455 | B2 | 12/2013 | Alexander et al. |
| 9,456,760 | B2 | 10/2016 | Hamatake |
| 2002/0173710 | A1 | 11/2002 | Licata |
| 2003/0139778 | A1 | 7/2003 | Fischell et al. |
| 2006/0142652 | A1 | 6/2006 | Keenan |
| 2008/0097429 | A1 | 4/2008 | McClurken |
| 2008/0161788 | A1 | 7/2008 | Dando et al. |
| 2009/0276020 | A1 | 11/2009 | Nee et al. |
| 2010/0022950 | A1 | 1/2010 | Anderson et al. |
| 2010/0222664 | A1 | 9/2010 | Lemon et al. |
| 2010/0228202 | A1 | 9/2010 | O'Dea et al. |
| 2010/0305673 | A1 | 12/2010 | Jolly et al. |
| 2010/0318095 | A1 | 12/2010 | Brushey |
| 2010/0331712 | A1 | 12/2010 | Rothenberg |
| 2012/0101496 | A1 | 4/2012 | McClurken et al. |
| 2014/0275918 | A1 | 9/2014 | Muse et al. |

FOREIGN PATENT DOCUMENTS

| | | |
|---|---|---|
| WO | 9424931 A1 | 11/1994 |
| WO | 2004065098 A1 | 8/2004 |
| WO | 2011005165 A1 | 1/2011 |
| WO | 2014160247 A1 | 10/2014 |
| WO | 2015/138876 A1 | 9/2015 |

OTHER PUBLICATIONS

PCT/US2015/020415 filed Mar. 13, 2015 Search Report dated Jun. 29, 2015.
U.S. Appl. No. 14/209,600, filed Mar. 13, 2014 Non-Final Office Action dated Mar. 17, 2016.
EP 14776561.4 filed Oct. 1, 2015 Partial European Search Report dated Oct. 26, 2016.
Pittiruti, et al. "The electrocardiographic method for positioning the tip of central venous catheters" JAVA, pp. 1-12, Feb. 12, 2011.
CN 201480011607.8 filed Aug. 31, 2015 Office Action dated Mar. 20, 2017.
EP 14776561.4 filed Oct. 1, 2015 Extended European Search Report dated Mar. 13, 2017.

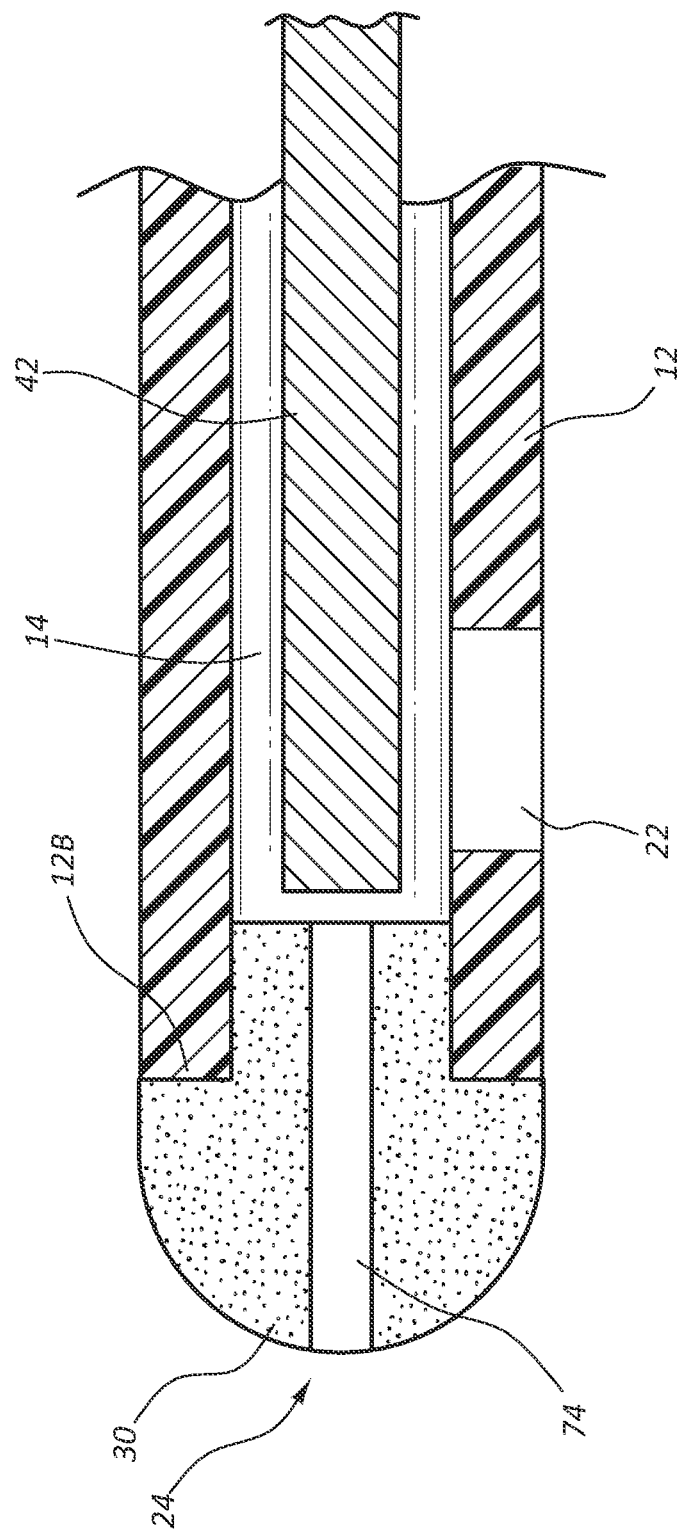

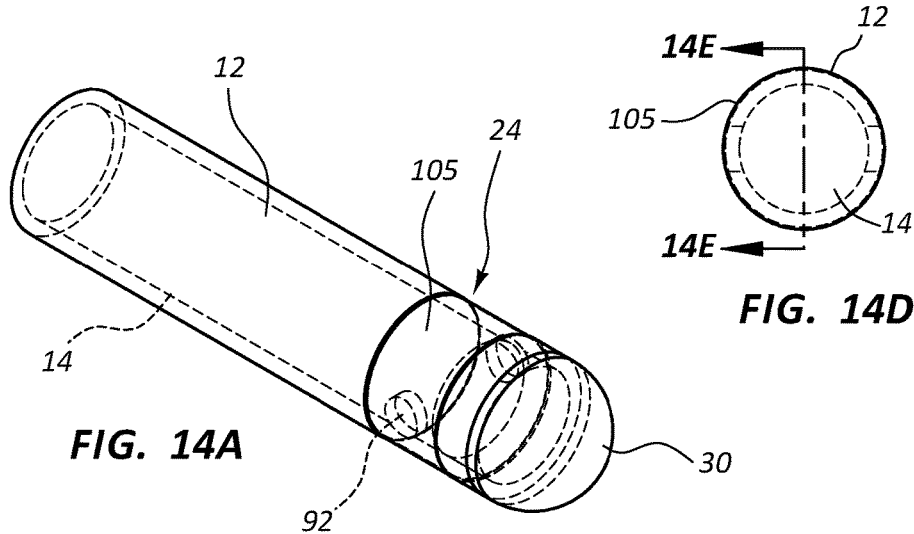
FIG. 14A
FIG. 14D
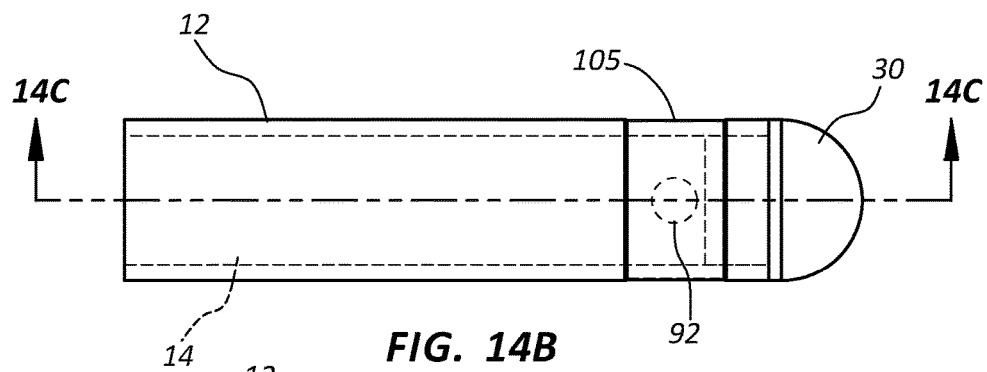
FIG. 14B
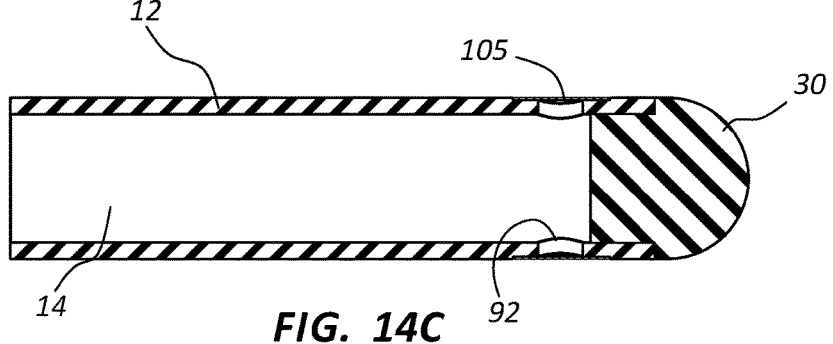
FIG. 14C
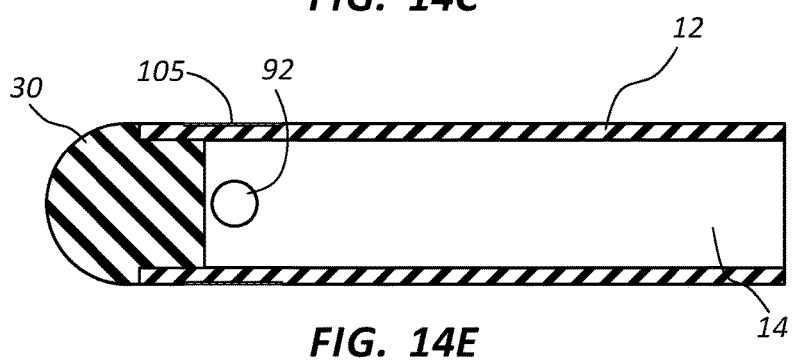
FIG. 14E

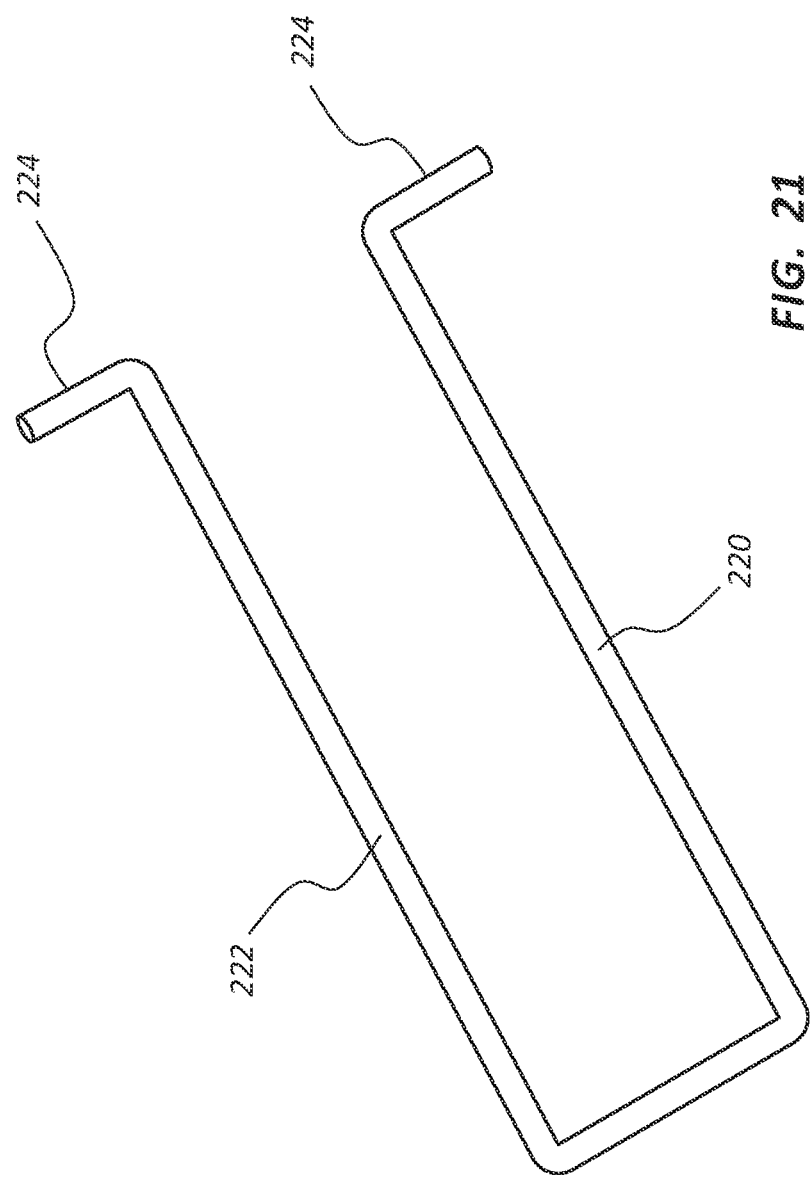

ELECTRICALLY CONDUCTIVE PATHWAY IN A CLOSED-ENDED CATHETER

CROSS-REFERENCE TO RELATED APPLICATIONS

This application is a continuation-in-part of U.S. patent application Ser. No. 14/209,600, filed Mar. 13, 2014, now U.S. Pat. No. 9,456,760, and titled "Closed Catheter Tip Including Electrically Conductive Pathway, which claims the benefit of U.S. Provisional Application No. 61/784,625, filed Mar. 14, 2013, and titled "Closed Catheter Tip Including Electrically Conductive Pathway." This application also claims the benefit of U.S. Provisional Application Nos. 61/952,813, filed Mar. 13, 2014, and titled "Apparatus for Providing an Electrically Conductive Pathway in a Closed-Ended Catheter," and 62/013,494, filed Jun. 17, 2014, and titled "Apparatus for Providing an Electrically Conductive Pathway in a Closed-Ended Catheter." Each of the aforementioned patent applications is incorporated herein by reference in its entirety.

BRIEF SUMMARY

Briefly summarized, embodiments of the present invention are directed to a generally closed-ended catheter assembly that includes an electrically conductive pathway. The conductive pathway enables electrical signals, such as ECG signals produced by signal generating nodes of the patient's heart, to pass through the closed-ended tip of the indwelling catheter while still preventing unintended fluid flow. Such catheter assemblies are suitable for use with ECG signal monitoring devices, for instance.

In one embodiment, therefore, a catheter assembly for placement in a body of a patient is disclosed and comprises an elongate catheter tube including a closed distal end. The catheter tube defines at least one lumen and includes a valve defined in the catheter tube that is configured to selectively enable fluids to pass therethrough. The catheter tube includes a conductive element that provides an electrically conductive pathway between the at least one lumen and an exterior portion of the catheter. The conductive element includes a porous material extending between the at least one lumen and the exterior portion of the catheter, the porous material being permeable to electrical signals and non-permeable to blood.

In another embodiment, a catheter assembly is disclosed and comprises an elongate catheter tube including a closed distal end. The catheter tube defines a lumen and includes a valve defined in the catheter tube that is configured to selectively enable fluids to pass therethrough. The catheter tube includes a conductive element that provides an electrically conductive pathway between the lumen and an exterior portion of the catheter. The conductive element includes an electrically conductive sleeve disposed within the lumen and is positioned proximate a hole defined in a catheter tube wall. The hole enables fluids in a vessel of the patient body in which the catheter tube is disposed to contact the sleeve.

These and other features of the present disclosure will become more fully apparent from the following description and appended claims, or may be learned by the practice of the disclosure as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 8 is a cross sectional view of a distal portion of a catheter tube according to one embodiment.

FIGS. 13A and 3B are various views of a conductive pathway for a catheter tube according to one embodiment;

FIGS. 14A-14E depict various views of a distal portion of a catheter tube including a conductive pathway according to one embodiment;

FIG. 21 is a perspective view of a conductive element according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to catheters and other tubular devices for use in establishing access to an internal portion of a patient's body. In particular, present embodiments are directed to catheters including generally closed distal tips and a slit valve or other opening proximate thereto in order to selectively enable fluid passage through the catheter. In accordance with one embodiment, a distal portion of the closed-ended catheter tip includes an electrically conductive pathway that enables electrical signals, such as ECG signals produced by signal generating nodes of the patient's heart, to pass through the closed-ended tip of the indwelling catheter tube while still preventing unintended fluid flow. In this way, such ECG signals may be conveyed or passed (also referred to herein as "transmitted") through the catheter to an ECG signal monitoring device operably connected to a proximal portion of the catheter residing outside of the body. Again, note that transmission of the ECG signals occurs even though the distal tip of the catheter desirably remains closed to typical fluid flow. Further details regarding one example of an ECG signal monitoring device can be found in U.S. Patent Publication No. 2011/0015533, filed Sep. 29, 2010, and entitled "Stylets for use with Apparatus for Intravascular Placement of a Catheter," which is incorporated herein by reference in its entirety.

Figure 1:
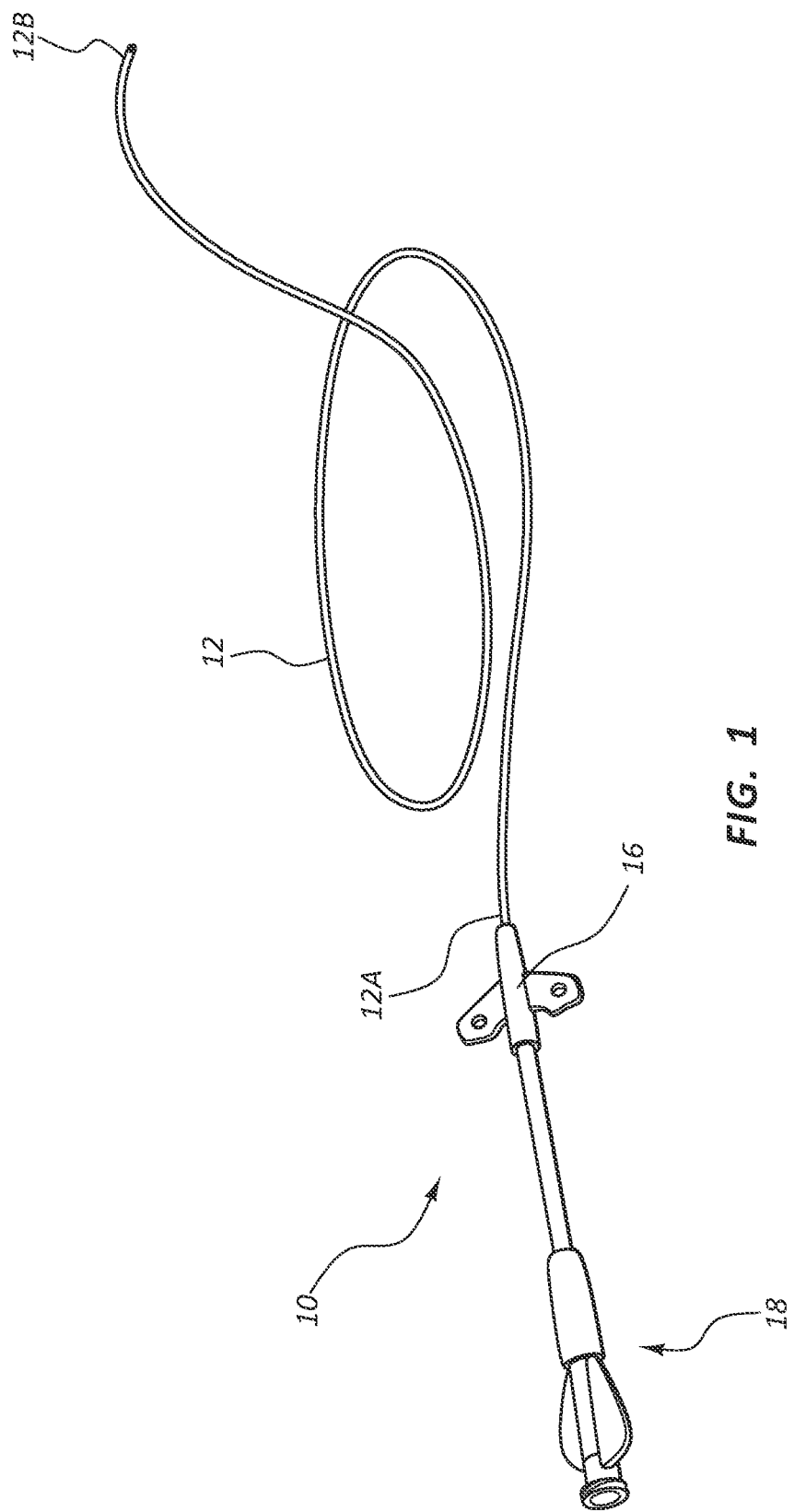
FIG. 1 is a perspective view of a catheter assembly according to one embodiment.

FIG. 1 shows a closed-ended catheter assembly ("catheter") 10 according to one embodiment, as an example device wherein embodiments described herein may be practiced. In detail, the catheter 10 is a GROSHONG® catheter manufactured by C. R. Bard, Inc., Murray Hill, N.J., and includes an elongate catheter tube 12 defining a proximal end 12A and a closed distal end 12B. A slit valve 22 (FIG. 2) is included proximate the distal end 12B of the catheter tube 12. The catheter 10 here includes a single lumen 14 (FIG. 2), though in other embodiments more than one lumen can be included. An extension leg 18 is operably attached to the proximal end 12A of the catheter tube 12 via a bifurcation 16. A distal plug 20 is inserted into the open distal end 12B of the catheter tube 12 during manufacture to close the distal end. In one embodiment, the catheter tube 12 and plug 20 include silicone, though other thermoset, thermoplastic, and other suitable materials can be used for these components. The catheter 10 described herein is configured for insertion into a blood-filled vasculature of the patient, though catheters can be used for other functions as well. Note that a variety of catheter types, brands, sizes, included slit or other valves, etc., can benefit from the principles described herein. In addition to a distal plug, other closure schemes for closing the distal end of the catheter tube are possible.

Figure 2:
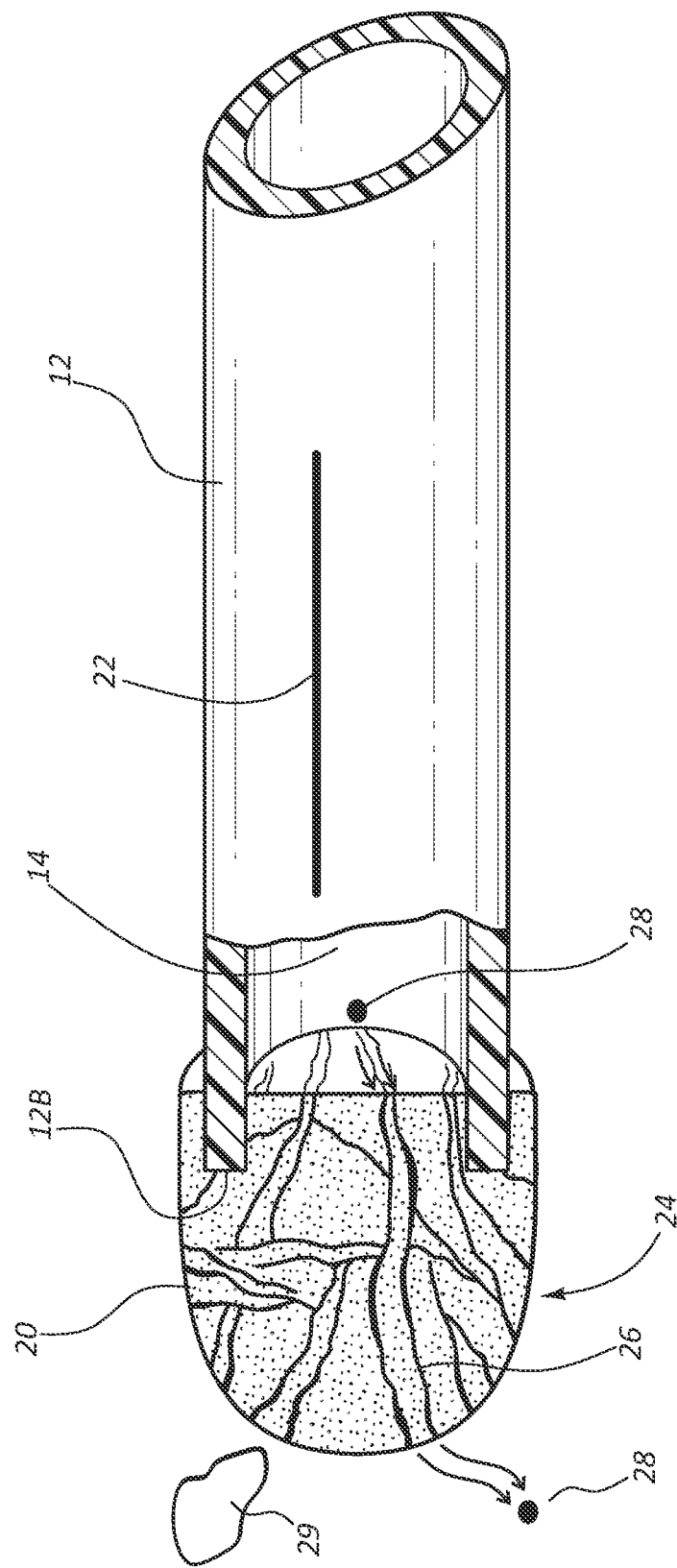
FIG. 2 is a cross sectional view of a distal portion of a catheter tube according to one embodiment.

FIG. 2 shows a distal portion of the catheter 10 including the catheter tube 12 and a slit valve 22 defined through the wall of the catheter tube such that it is selectively openable to enable fluid transfer to/from the lumen 14 when a sufficient pressure differential exists across the valve. Note that other slit valves and valve configurations can be employed with the catheter tube 12. The distal plug 20 is shown attached to the distal end 12B of the catheter tube 12 so as to close the tube and define a distal end of the tube and the lumen 14 defined thereby.

In the present embodiment depicted in FIG. 2, the catheter 10 further includes a conductive element 24 that provides an electrically conductive pathway for enabling electrical signals to pass between the lumen 14 and the exterior of the catheter 10. As shown, the conductive element 24 of the present embodiment includes the distal plug 20 that closes the lumen 14. Specifically, the distal plug 20 includes a material including micron-sized micropore (microporous) channels 26 that extend in an interconnected, network-like manner through the plug material. The size of the micropores 26 enables the passage of ions 28, and thus electrical signal passage, between the blood within the vasculature in which the indwelling catheter 10 is disposed and the interior of the lumen 14 where a conductive stylet (FIG. 3) or conductive liquid such as saline is present. The micropore channels 26, however, are small enough to prevent the passage of blood cells 29 therethrough, thus preventing fluid leakage through the plug 20. Note that the sizes of the ions 28 and blood cells 29 are not drawn to scale relative the catheter tube 12 in FIG. 2.

In one embodiment, suitable polymeric materials are used to form the micropore plug material. As mentioned, characteristics of a plug material suitable for the above purpose include the ability to enable electrical signals to pass while preventing fluid flow therethrough. As discussed, this is achieved in the present embodiment by forming the plug from a material that includes suitably small, interconnected or discrete channels through the material, porous material, sponge-like material, etc. The materials mentioned herein are therefore not to be considered limiting.

In another embodiment, a silicone foam material can be used to form the plug 20 and thus define the conductive element 24. The silicone foam facilitates ease of attachment to the distal end 12B of the catheter tube in the case where the catheter tube includes silicone as well. So configured, the foam material of the plug 20 acts like a sponge and provides a fluid-filled conductive pathway between the exterior surface of the plug 20 and the interior lumen 14. Conductive saline present in the catheter tube lumen 14 can infiltrate into foam material of the plug 20 to provide the conductive pathway between the lumen and the catheter tube exterior. One supplier of such material is Filtrona Porous Technologies, Colonial Heights, Va.

In yet another embodiment, a salt solution or other conductive fluid can be impregnated into or absorbed by the foam or other suitable material of the plug 20 prior to insertion of the catheter 10 into the patient vasculature to enhance electrical conductivity.

As with the other embodiments described herein, the conductive element 24 enables electrical signals, such as ECG signals from the patient's heart, to pass through the indwelling catheter tube 12, via the conductive element, into the catheter tube lumen 14, thus forming the aforementioned conductive pathway. These signals can then pass proximally up through the catheter tube 12 and extension leg 18 to the proximal end of the catheter 10 via conductive solution disposed in the lumen, a stylet disposed in the lumen, or by another suitable configuration. These signals can then be received by an ECG signal monitoring device, as discussed. A suitable connector or interface can be employed to operably connect the stylet, conductive solution, etc., to the signal monitoring device, such as a luer connector securable to the extension leg connector that attaches to the stylet.

Note that the conductive elements discussed herein can include one, two, or more components that cooperate to provide an electrically conductive pathway through the catheter.

Figure 3:
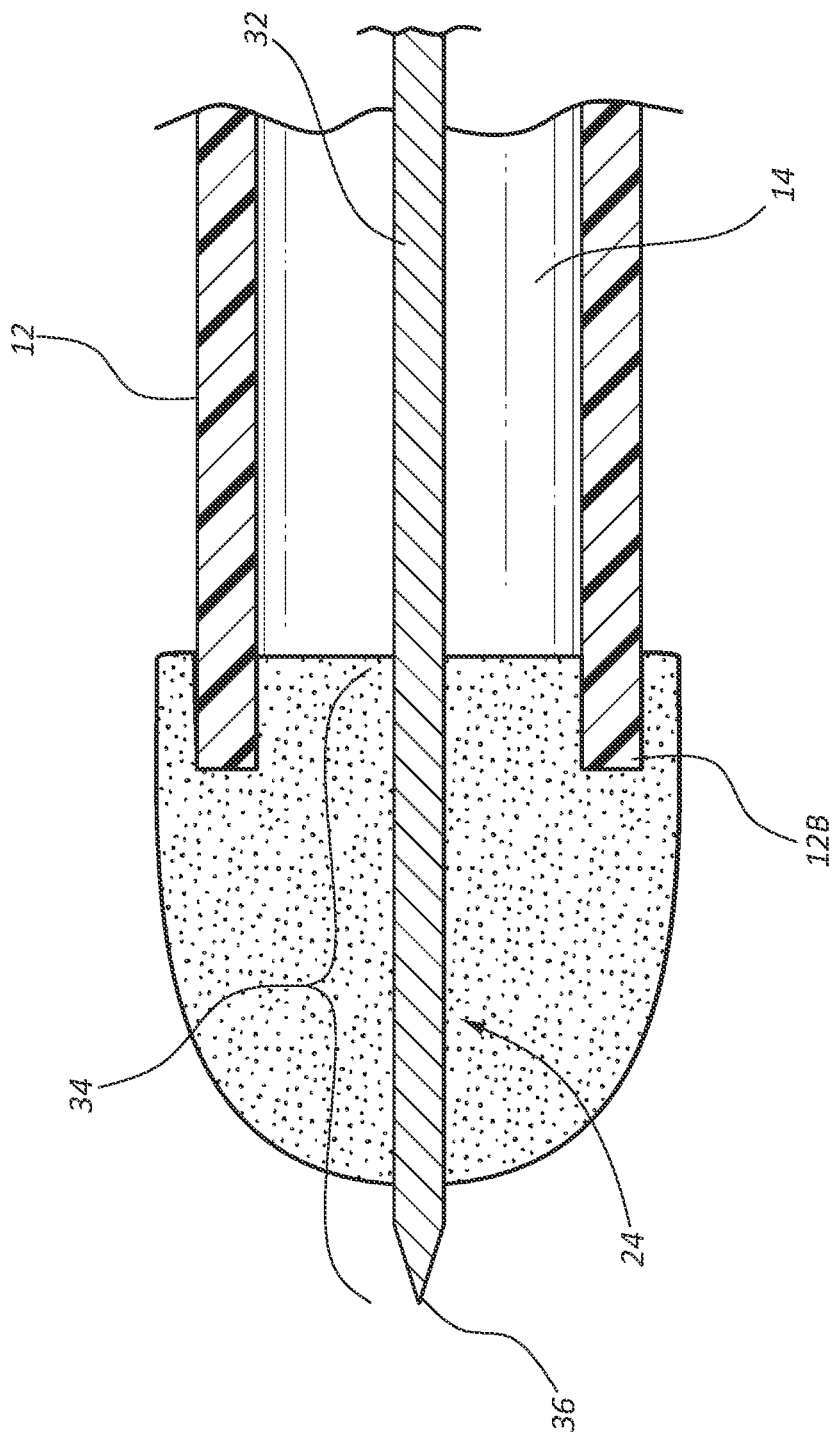
FIG. 3 is a cross sectional view of a distal portion of a catheter tube according to one embodiment.

FIG. 3 shows a distal portion of the catheter 10 according to one embodiment, including another example of the conductive element 24 for providing an electrically conductive pathway through the catheter tube. As shown, a distal portion 34 of an electrically conductive stylet 32 is inserted into the lumen 14 of the catheter tube 12 and is distally advanced sufficient to cause a sharpened distal tip 36 thereof to pierce and extend from a compliant distal plug 30 of the catheter tube. This establishes an electrically conductive pathway from the lumen 14 interior to the exterior of the catheter 10. Once the conductive pathway is no longer needed, the stylet 32 can be pulled proximally by a user such that the stylet distal portion 34 and tip 36 are disengaged from the plug 30. The compliant plug 30 includes silicone or other suitable self-sealing material such that the hole created by the stylet piercing seals to prevent fluid passage therethrough. In one embodiment, the stylet includes stainless steel, though other suitable, conductive stylet materials can also be used.

Figure 4:
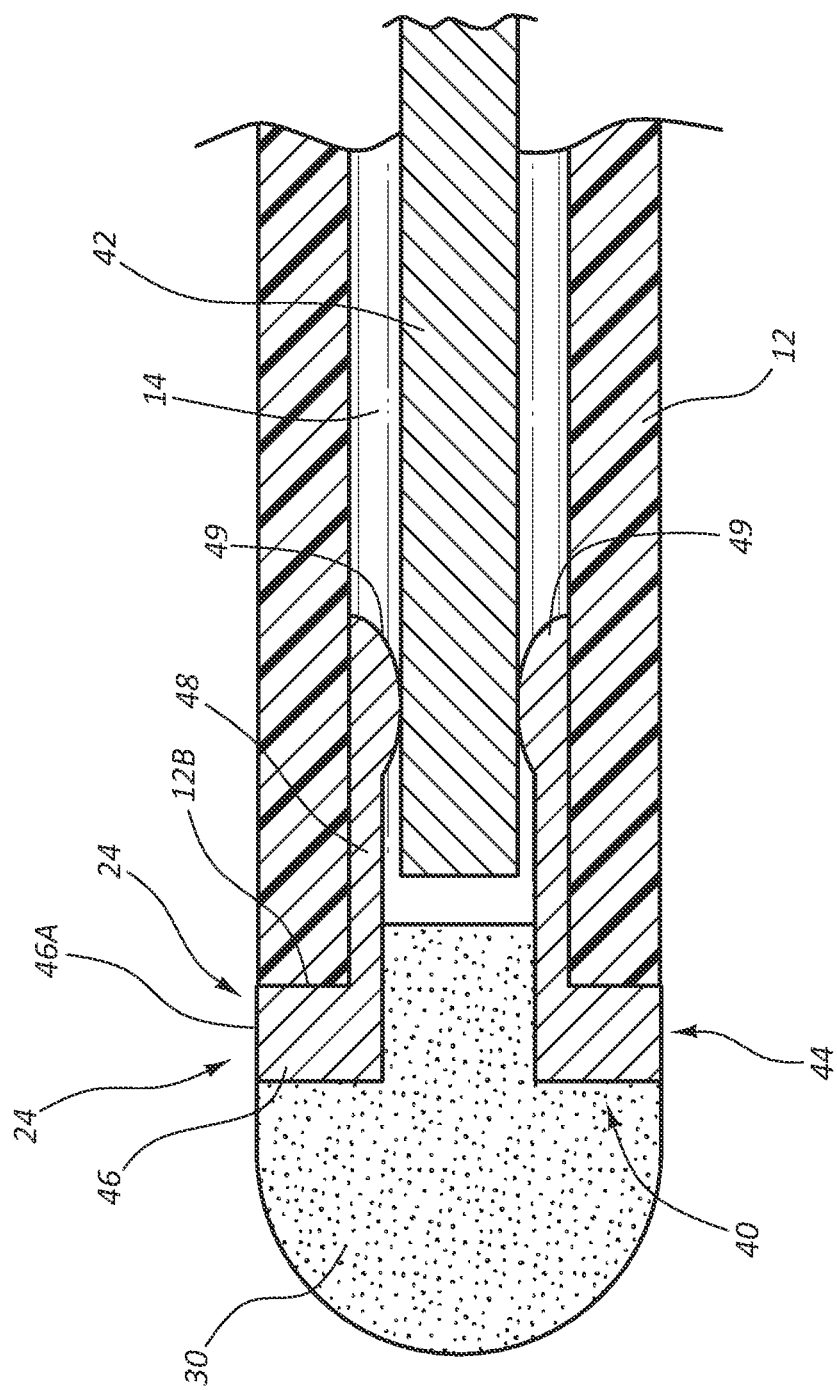
FIG. 4 is a cross sectional view of a distal portion of a catheter tube according to one embodiment.

FIG. 4 shows a distal portion of the catheter 10 including the conductive element 24 to provide an electrically conductive pathway according to another embodiment. As shown, the conductive element 24 includes a conductive insert 44 that is interposed between the plug 30 and the distal end 12B of the catheter tube 12 (though other insert configurations and locations are also possible along the catheter tube). The insert 44 includes a sleeve-shaped outer portion 46 that includes an outer surface 46A that is external to the catheter 10, and a cylindrically-shaped inner portion 48. An inner surface of the cylindrical inner portion 48 includes one or more protuberances 49 so as to facilitate physical coupling of the inner portion with a conductive stylet 42 disposed within the catheter tube lumen 14. In another embodiment, the inner portion 48 can electrically couple with conductive saline or other suitably conductive solution disposed in the lumen. Thus, a conductive pathway is provided through the catheter via the outer portion 46 and the inner portion 48 of the insert 44.

Figure 5:
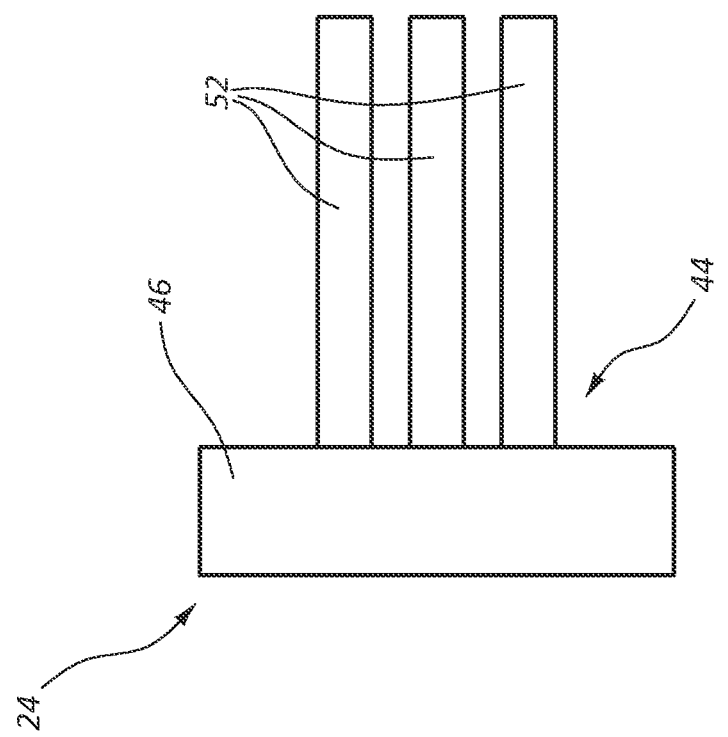
FIG. 5 is a side view of a conductive catheter insert according to one embodiment.

FIG. 5 shows the conductive insert 44 according to another embodiment, wherein the inner portion of the insert includes a plurality of contact arms 52 that can extend proximally within the lumen 14 of the catheter tube 12 (FIG. 5) and are configured to conductively contact the lumen-inserted stylet 42 or conductive liquid disposed therein so as to provide a conductive pathway through the catheter tube 12. It is thus appreciated that both the outer and inner portions of the conductive insert can include one of a variety of configurations.

Figure 6:
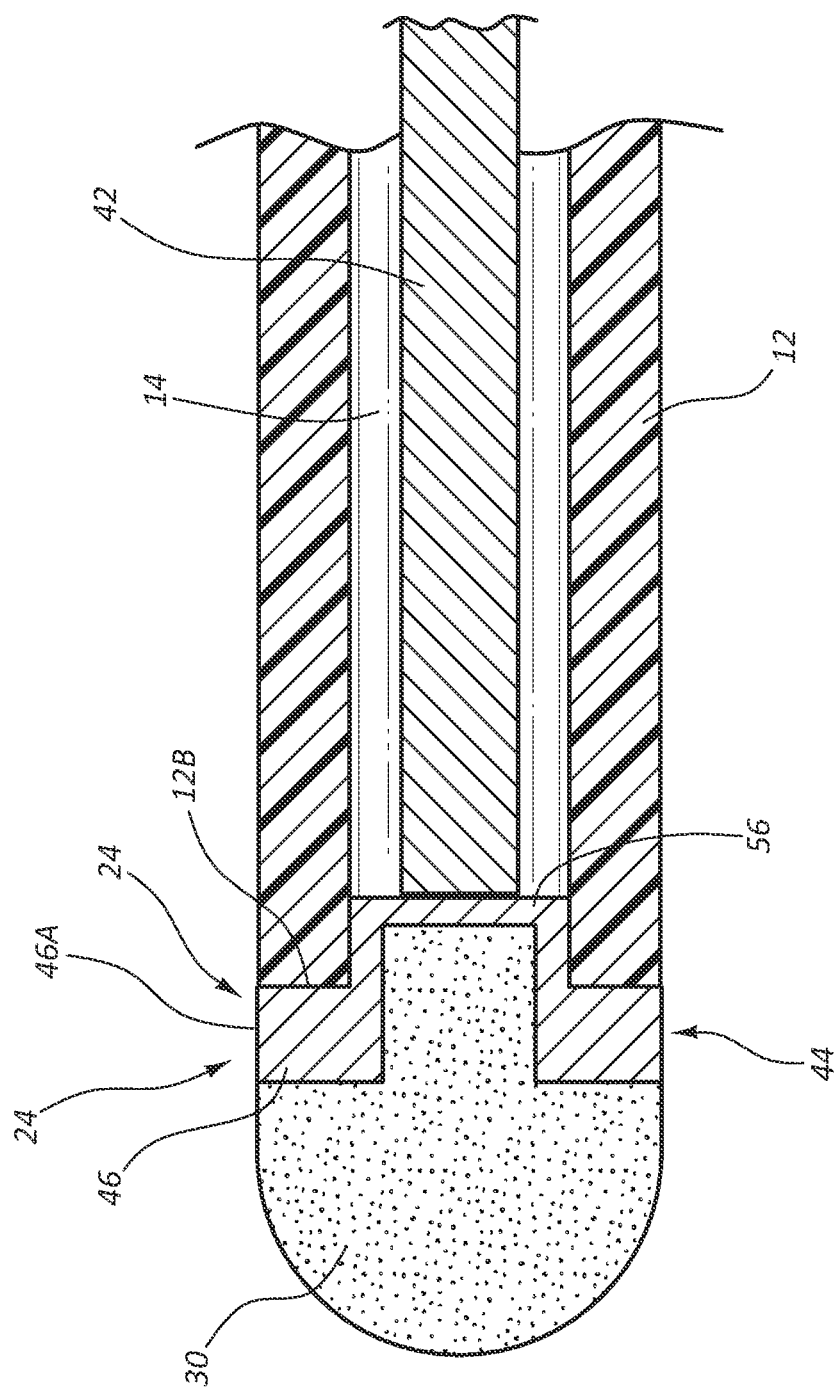
FIG. 6 is a cross sectional view of a distal portion of a catheter tube according to one embodiment.

FIG. 6 shows the conductive insert 44 according to another embodiment, wherein the inner portion of the insert includes a disk 56 that is disposed adjacent a proximal end of the distal plug 30. The disk 56 is configured to conductively contact the lumen-inserted stylet 42 or conductive liquid disposed therein so as to provide a conductive pathway through the catheter tube 12. The thickness, size, shape, etc., of the disk can vary from what is shown and described herein.

Figure 7:
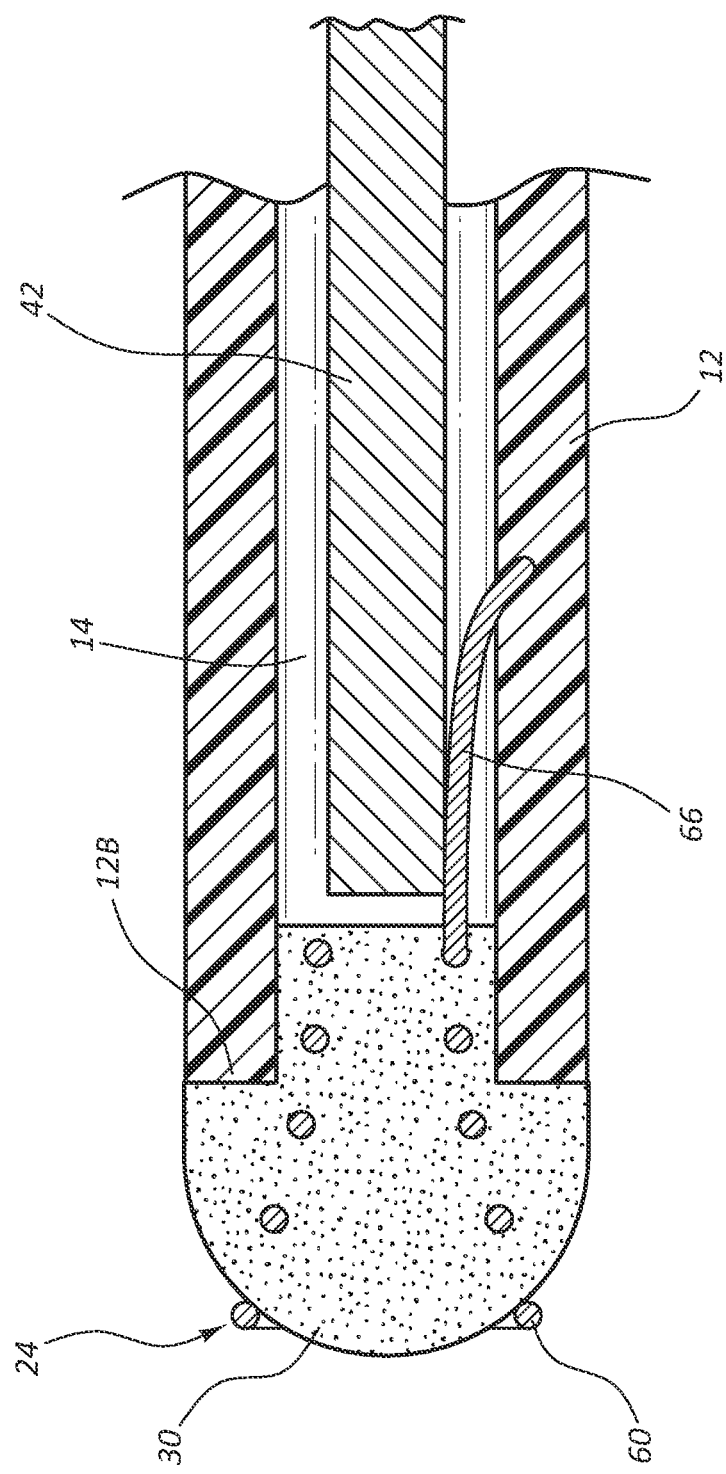
FIG. 7 is a cross sectional view of a distal portion of a catheter tube according to one embodiment.

FIG. 7 shows a distal portion of the catheter 10 including the conductive element 24 to provide an electrically conductive pathway according to another embodiment. As shown, the conductive element 24 includes a conductive coil 60 that is incorporated into the distal plug 30 such that a portion thereof extends to the exterior portion of the catheter proximate the distal end thereof. The coil 60 further includes an inner contact arm 66 that is configured to physically and conductively contact the stylet 42 when disposed in the catheter tube lumen 14 so as to establish a conductive pathway between the exterior of the catheter and the interior of the lumen. Again, and as with other embodiments, a conductive fluid can be disposed in the lumen 14 in addition to or instead of the stylet 42, in one embodiment.

FIG. 8 shows a distal portion of the catheter 10 including the conductive element 24 to provide an electrically conductive pathway according to another embodiment. As shown, the conductive element 24 includes a conduit 74 defined at time of catheter manufacture longitudinally through the distal plug 30. When initially placed within the patient vasculature, the conduit 74 is open, enabling fluid transfer, and thus electrical signal passage, between the vessel in which the catheter tube is disposed and the catheter tube lumen 14. After a short period of time with the catheter indwelling within the vasculature, the conduit 74 will be filled with thrombus formed by the body, thus thereafter preventing fluid flow therethrough. Thus, the conductive pathway is available during, and for a relatively short time after, catheter tube insertion into the patient vasculature so that ECG signal monitoring or other conductively related activities may occur. Note that the size, location, and configuration of the conduit 74 can vary from what is shown here. Note also that, though the conduit 74 provides an open pathway for a limited time to the lumen 14, the catheter 10 in the present embodiment can still be considered a generally closed catheter due to the fact that the conduit will be occluded by thrombus not long after insertion of the catheter into the patient body. In one embodiment, note that the conduit can be defined in other portions of the catheter tube, such as through the side wall of the catheter tube, in one example.

Note further that FIG. 8 further shows one example of a slit valve 22 and its position with respect to the distal end of the catheter tube 12. It is appreciated that in one embodiment, the valve is disposed proximal to the conductive element, though in other embodiments it may be disposed distal to the conductive element.

Figure 9A:
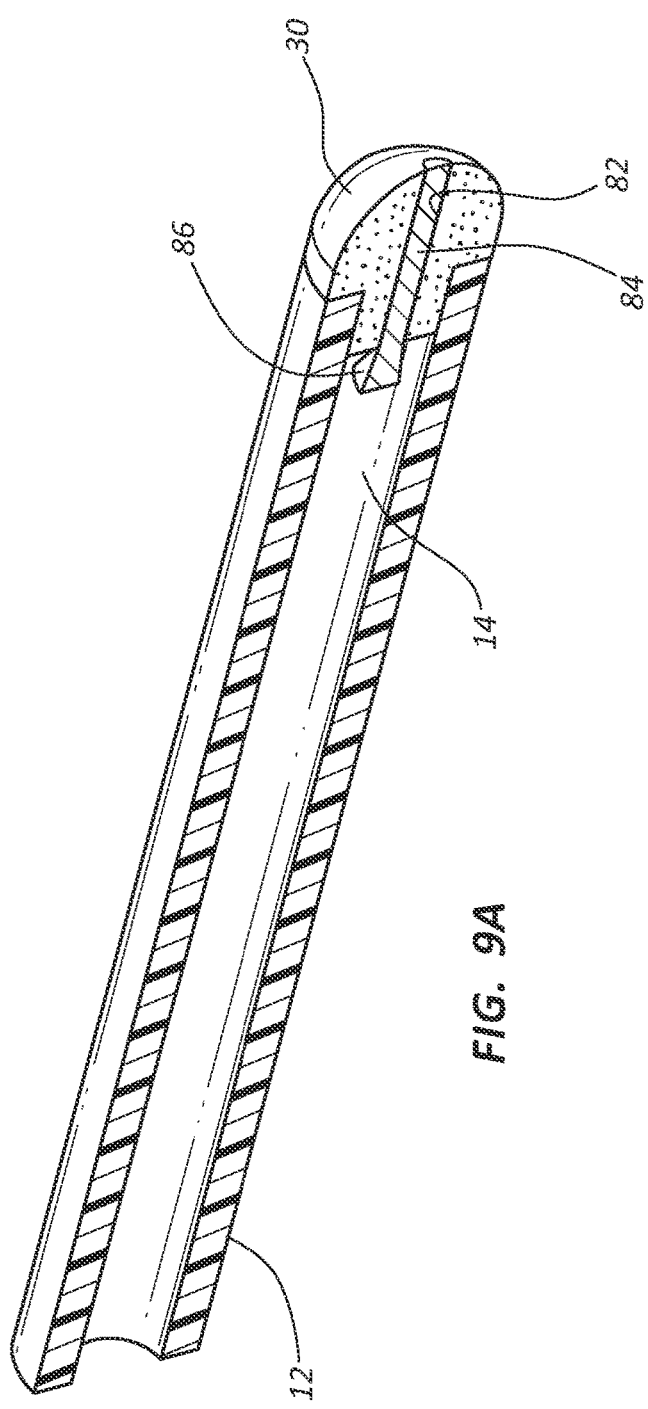
FIGS. 9A-9C are various views of a distal portion of a catheter tube according to one embodiment.
Figure 9C:
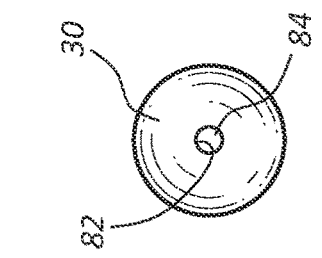
Figure 9B:
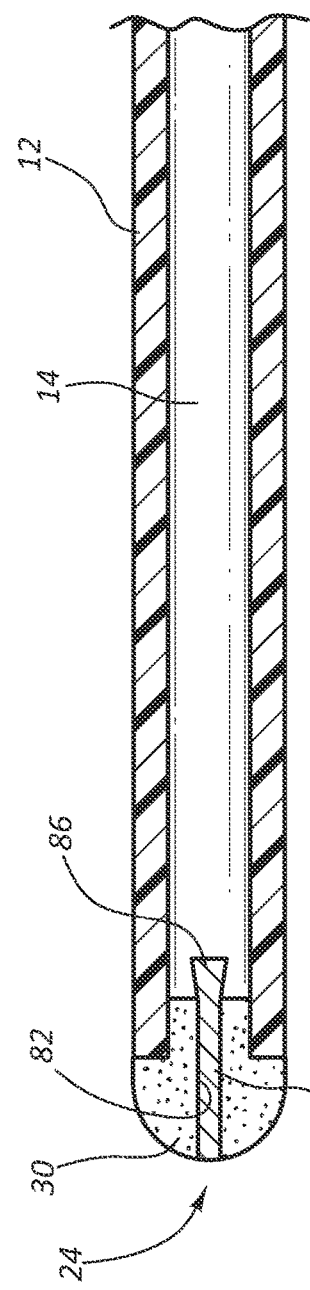

FIGS. 9A-9C show a distal portion of the catheter tube 12 including the conductive element 24 to provide an electrically conductive pathway according to another embodiment. As shown, the conductive element 24 includes a conduit 82 defined at time of catheter manufacture longitudinally through the distal plug 30. A wick 84 is permanently disposed in the conduit 82 such that an extended portion 86 extends proximally into the catheter tube lumen 14 to ensure adequate contact of the wick with the conductive solution disposed within the lumen 14 or with a stylet. So configured, the wick 84 absorbs normal saline or other conductive solution disposed within the lumen 14 such as via capillary action so as to desirably provide a conductive pathway between the lumen and the exterior of the catheter tube 12 via the wick.

The wick 84 in one embodiment includes a suitable material, including wicking yarn, porous fibrous plastic, etc. In one embodiment, the wick material is natively, or treated to be, hydrophilic. In one embodiment, the wick is temporarily disposed in the hole conduit 82 so as to be removable therefrom. In one embodiment, the wick is dissolvable. In yet another embodiment, the wick includes no extended portion. In a further embodiment, the wick extends beyond the distal end of the distal plug 30 during the manufacturing process and can be trimmed so as to be flush with the distal plug surface.

Note that, though the wick 84 enables some fluid transfer from/to the lumen to provide a conductive pathway, the catheter 10 in the present embodiment can still be considered a generally closed catheter due to the fact that the fluid transfer is substantially slow compared to normal fluid transfer via the catheter slit valve.

Figure 10A:
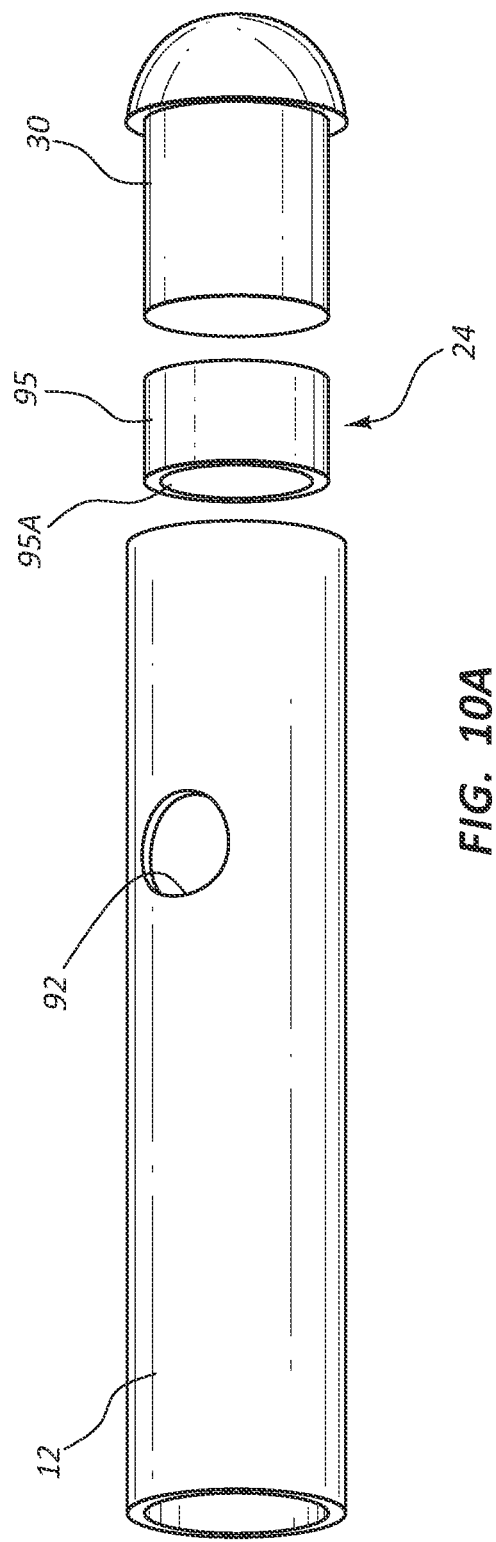
FIGS. 10A and 10B are various views a distal portion of a catheter tube including a conductive pathway according to one embodiment.
Figure 10B:
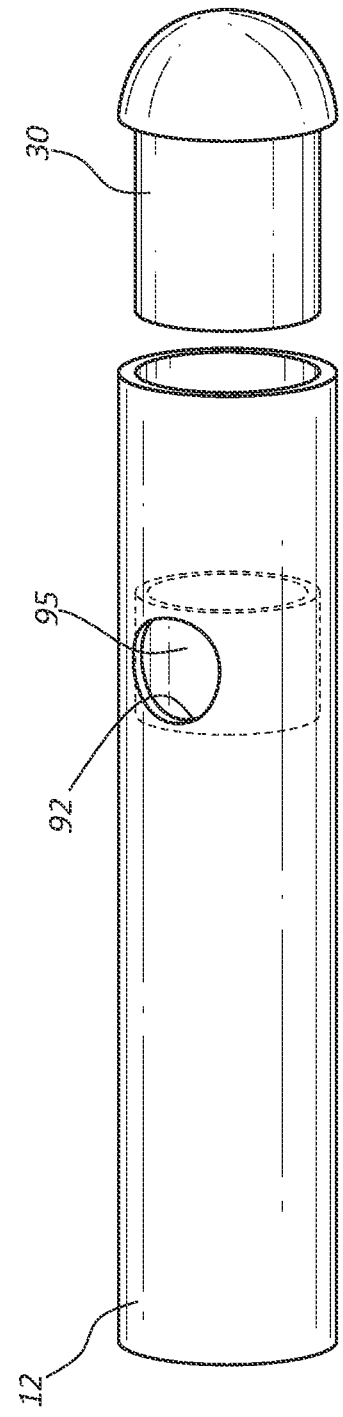

FIGS. 10A and 10B show a distal portion of the catheter 10 including the conductive element 24 to provide an electrically conductive pathway in the closed-ended catheter tube 12 for enabling electrical signals to pass between the lumen 14 and the exterior of the catheter according to another embodiment. As shown, the conductive element 24 of the present embodiment includes an internal sleeve 95 that is disposed within the lumen 14 of the catheter tube 12. The sleeve 95 includes a hollow core 35A to enable fluid passage therethrough and is disposed within the lumen 14 adjacent one or more holes 92 defined through the wall of the catheter tube 12 to enable fluids present in the vessel in which the catheter tube 12 is disposed to contact the sleeve 95. In this way, a conductive pathway is defined between the exterior of the catheter and the internal catheter lumen to enable the passage of ECG or other electrical signals therethrough while preventing fluid transfer through the hole 92. The sleeve 95 includes a conductive metal, such as stainless steel, in one embodiment, and can be secured within the lumen 14 by an adhesive, via insert molding, or by securement by or with the distal plug 30 when the distal plug is inserted or otherwise disposed in the distal end of the catheter tube 12. For instance, in one embodiment the distal plug 30 is formed by injecting liquid silicone into the distal end of the catheter tube 12. In this case, a portion of the distal plug 30 can form about a portion of the internal sleeve 95 while still fluid enough to do so, thus securing the sleeve in place. This securement can also be employed in other embodiments described herein.

Figure 11:
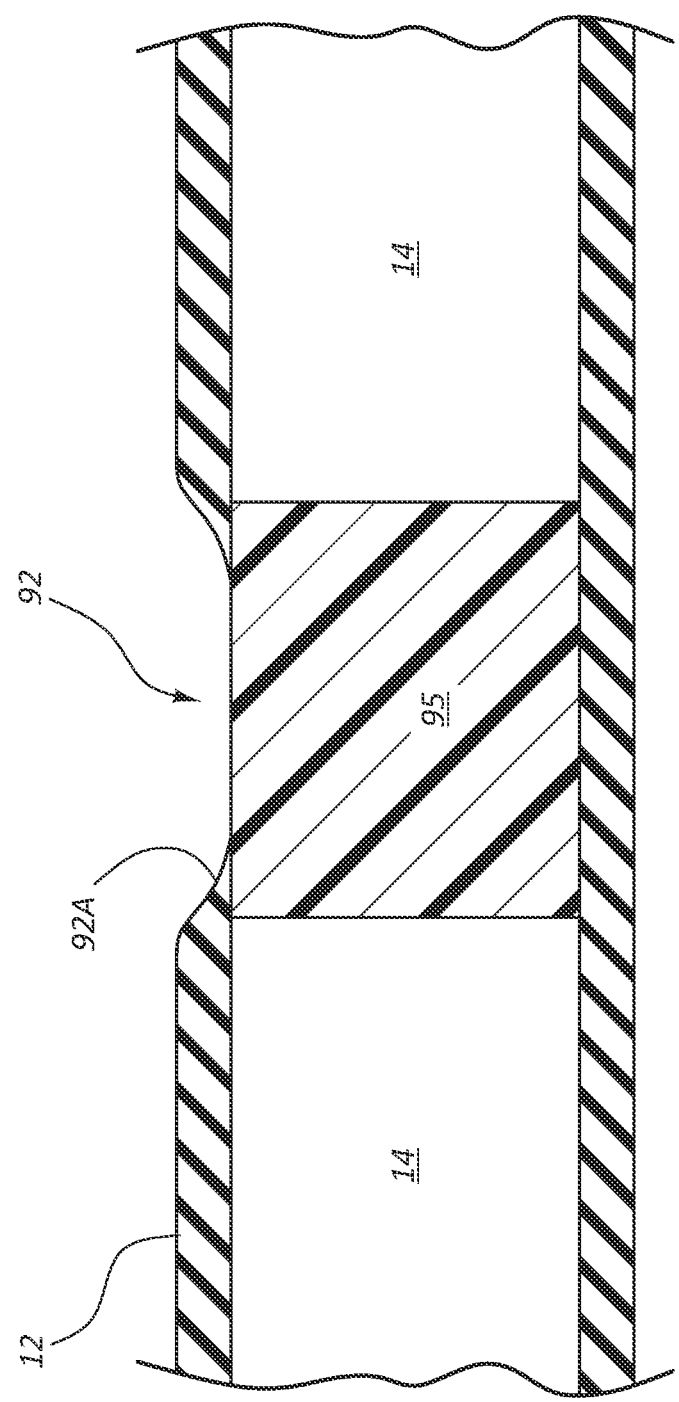
FIG. 11 is a cross-sectional view of the conductive pathway of the catheter tube of FIGS. 10A and 10B.

FIG. 11 shows that, in one embodiment, a perimeter 92A of the hole 92 shown in FIGS. 10A and 10B can be shaped to a tapered (e.g., rounded) profile instead of an abruptly angular shape. Such a tapered profile can be achieved in one embodiment by skiving the hole 92 via drilling at a substantially tangential angle to the outer surface of the catheter tube 12 or by another suitable process to define the hole. In another embodiment, laser ablation can be employed to define the hole 92 and its tapered perimeter 92A.

The tapered profile of the hole perimeter 92A prevents air bubbles from adhering to the hole 92 while the catheter tube 12 is disposed within the bloodstream of the patient, thus ensuring that electrical signals from the patient can be acceptably transmitted from the blood to the internal sleeve 95 via the hole. The tapered profile can be concavely shaped, as in the present embodiment. Note that various tapered profiles of the hole 92 can be utilized and that less than the entirety of the hole is tapered. Note also that hole shapes other than circular may be employed.

Figure 12A:
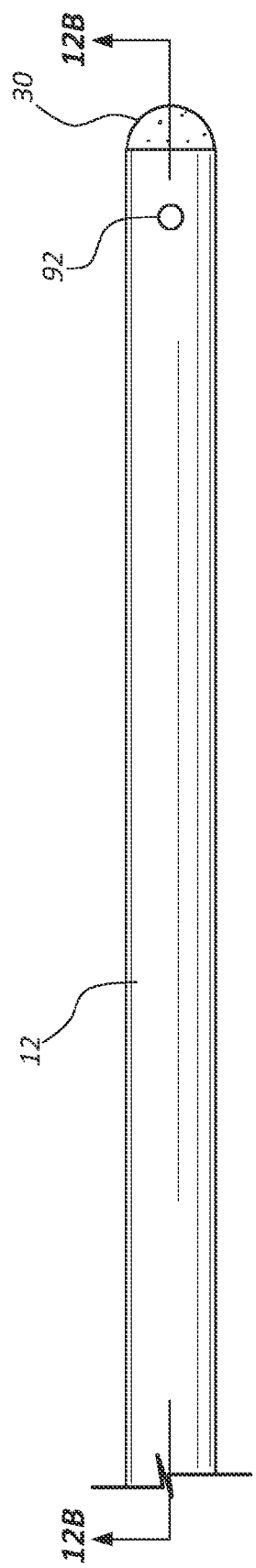
FIGS. 12A and 12B are various views of a distal portion of a catheter tube including a conductive pathway according to one embodiment.
Figure 12B:
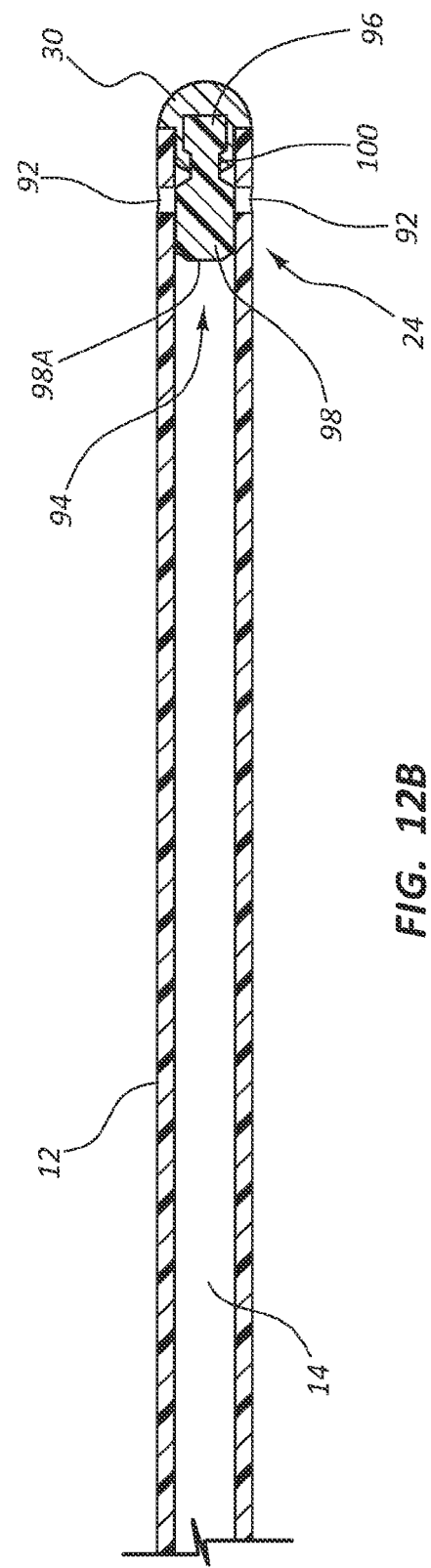

FIGS. 12A and 12B show a distal portion of the catheter tube 12 including the conductive element 24 to provide an electrically conductive pathway according to another embodiment. As shown, the conductive element 24 includes a solid-body, plug-like conductive insert 94 that is inserted into a distal portion of the catheter tube 12. The conductive insert 94 here includes a first portion 96 that is disposed within a portion of the distal plug 30, a second portion 98 that is disposed within the catheter tube lumen 14, and a neck 100 that interconnects the two portions. An abutting surface 98A is included on a proximal end of the second portion 98 to enable a stylet disposed in the lumen 14 to abut and physically contact the insert 94 to enable the transfer of electrical signals, in one embodiment. Holes 92 are defined through the wall of the catheter tube 12 to enable blood or other fluids present in the vessel in which the catheter tube is disposed to contact the conductive insert 94 to enable electrical signal transfer. The conductive insert 94 includes an electrically conductive material, such as stainless steel or other suitable metal, in one embodiment.

Figure 13B:
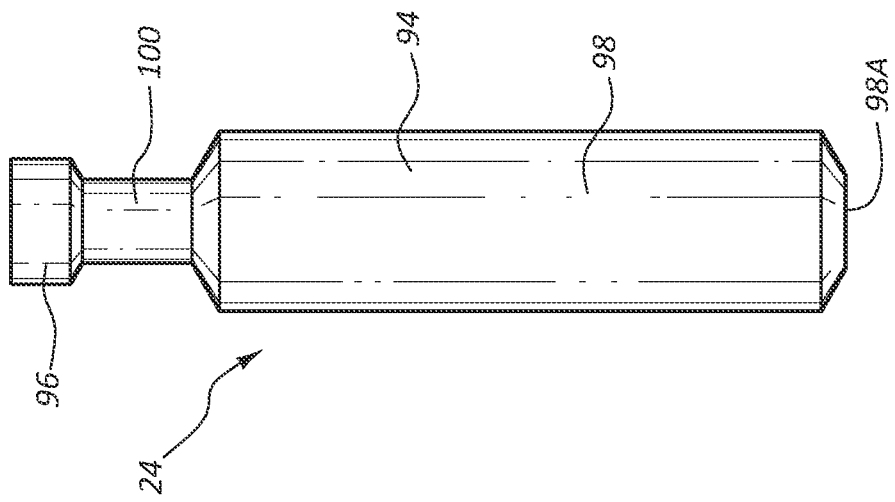
Figure 13A:
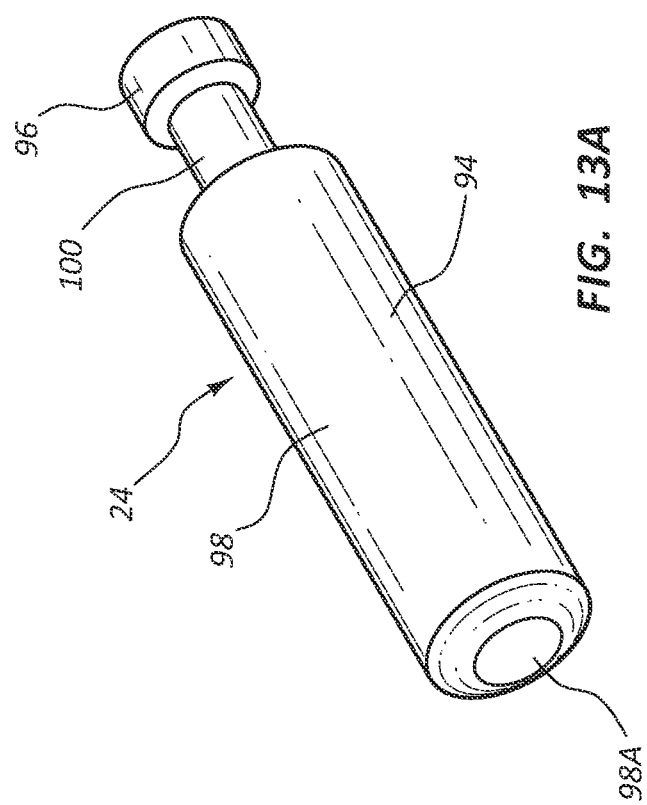

The conductive insert can include one of a variety of shapes, sizes, positions, configurations, etc. FIGS. 13A and 13B show one example of this according to one embodiment, wherein the conductive insert 94 includes a relatively long second portion 98. These and other modifications are therefore contemplated.

FIGS. 14A-14E show various views of a distal portion of the catheter tube 12 including the conductive element 24 to provide an electrically conductive pathway according to another embodiment, wherein the conductive element includes an external sleeve 105 that is disposed over an external portion of the catheter tube 12 so as to cover one or more of the holes 92 disposed in the wall of the catheter tube. In one embodiment, the external sleeve 105 is slipped over the distal end of the catheter tube 12 so as to cover the holes(s) 92, then swaged or crimped so as to be retained in place over hole(s). As discussed earlier, the hole(s) 92 may include a rounded or tapered perimeter to prevent the formation of air bubbles thereon. In one embodiment, the external sleeve 105 is swaged or crimped so as to define an outer diameter that is substantially the same or slightly less than the outer diameter of the catheter tube 12.

With the conductive element 24 so configured, electrical signals can pass from blood or other fluids in which the catheter tube 12 is disposed, through the external sleeve 105 and hole(s) 92, and into the fluid or stylet-filled lumen 14, as desired. As before, the external sleeve 105 includes an electrically conductive material, such as stainless steel, titanium, a titanium alloy, or other suitable metals or metal alloys, in one embodiment.

Figure 15:
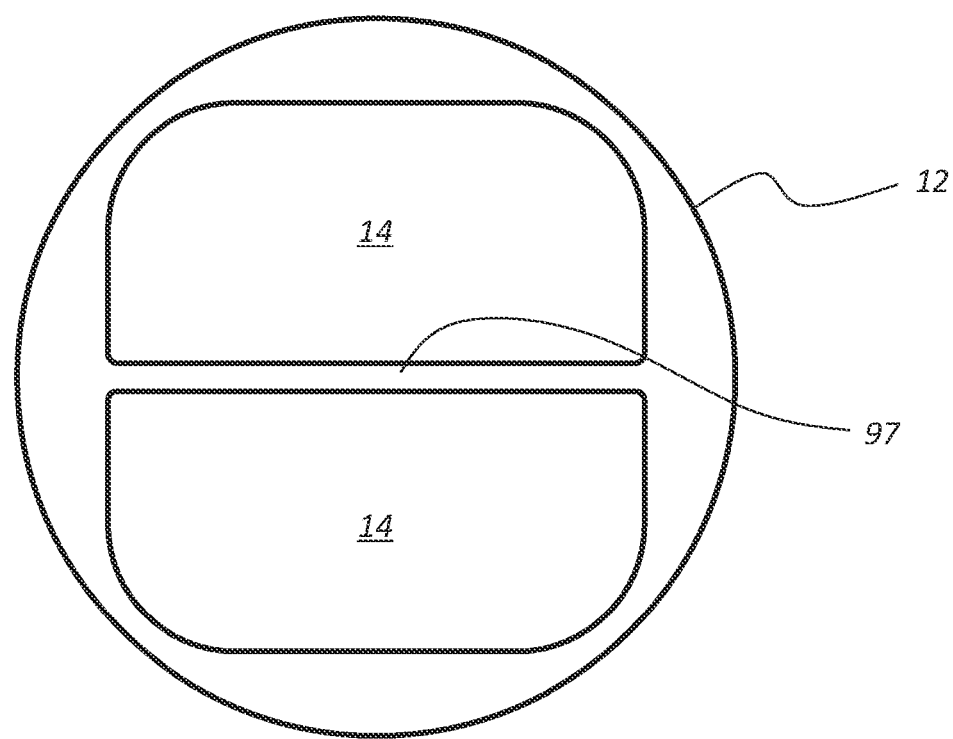
FIG. 15 is a cross-sectional view of a dual-lumen catheter.
Figure 16:
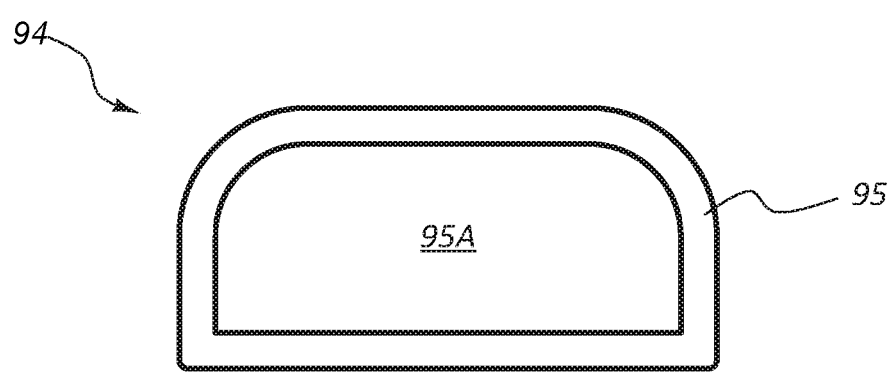
FIG. 16 is a cross-sectional view of a conductive element for one of the lumens shown in FIG. 15.

FIG. 15 shows a cross sectional of the catheter tube 12 of a dual-lumen catheter according to one embodiment, wherein the lumens 14 defined by the tube each approximately define a D-shape. Accordingly, FIG. 16 shows the conductive insert 94 implemented as the internal sleeve 95 including the hollow core 95A and being correspondingly shaped in an approximate D-shape so as to be suitably disposed within one of the lumens 14 of the catheter tube 12 shown in FIG. 15. As such, this illustrates that the shape and configuration of the conductive insert can vary according to catheter design.

Figure 17:
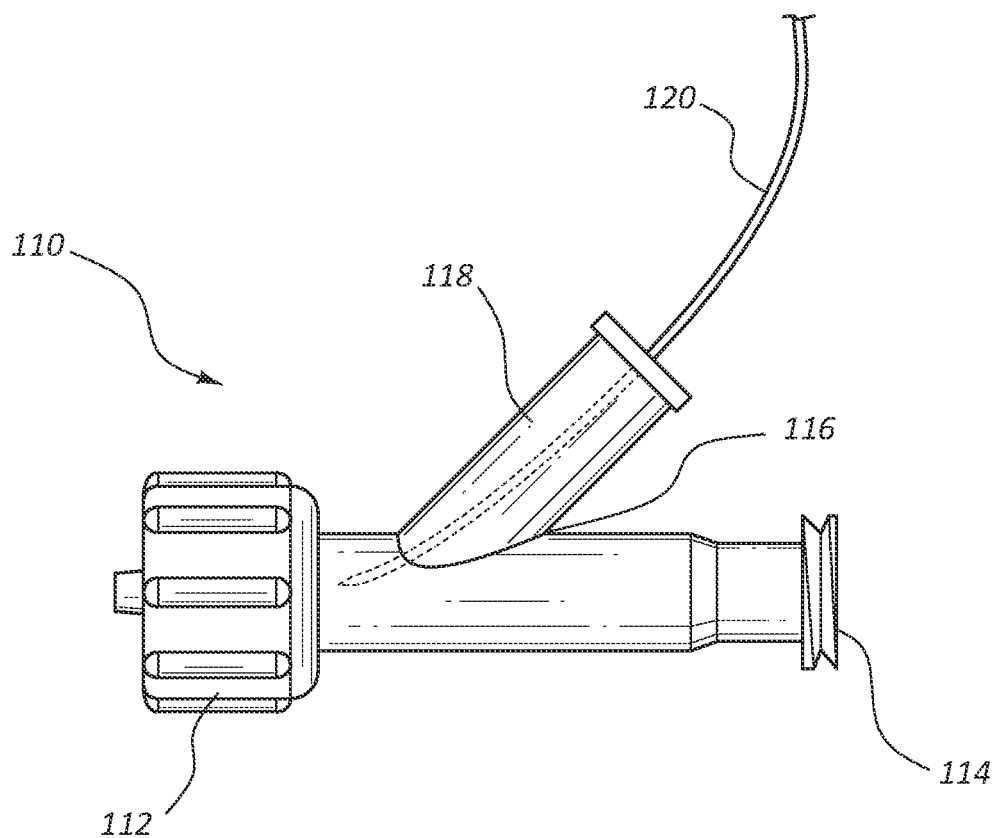
FIG. 17 is a simplified side view of an extension leg connector for providing a conductive pathway according to one embodiment.

FIG. 17 shows that, in one embodiment, a connector assembly 110 can be employed to establish a conductive pathway through one lumen of a multi-lumen catheter. As shown, the connector assembly 110 includes a male luer connector 112 for attaching the assembly to a proximal end of one of the extension legs of the catheter. A female luer connector 114 is also included and defines a port through which saline or other liquid can be injected into the extension leg and catheter tube lumen. The bifurcation branch leads to another port through which a conductive wire 120 can be inserted and distally advanced sufficient to place the wire into fluid communication with saline or other liquid in the extension leg and corresponding lumen of the catheter tube. The conductive wire 110, saline present in the extension leg and corresponding catheter lumen, and a conductive element disposed proximate the distal end of the closed catheter lumen (as described in the embodiments herein) provide a conductive pathway through which ECG signals can be passed from within the patient to an ECG monitoring device or other component external to the patient.

Figure 18:
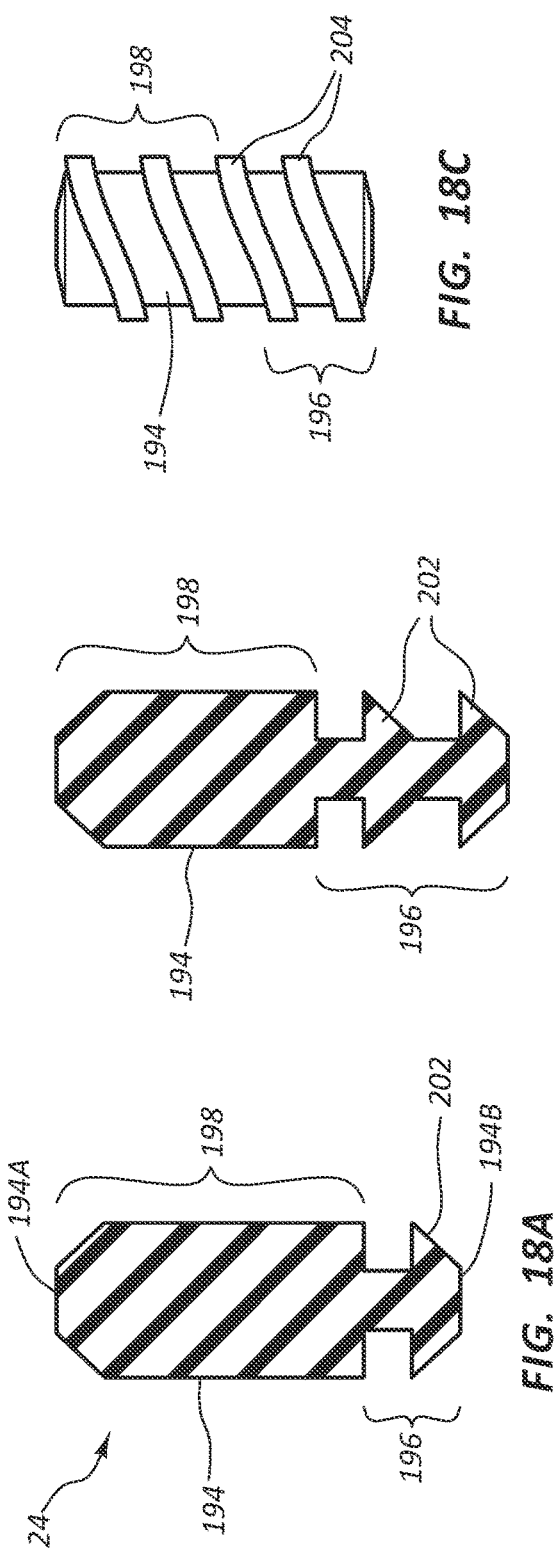
FIGS. 18A-18F are various views of conductive elements according to various embodiments.

FIGS. 18A-18F give views of various examples of the conductive element 24 to provide an electrically conductive pathway in a closed-ended catheter tube for enabling electrical signals to pass between the lumen and the exterior of the catheter according to example embodiments. FIG. 18A shows the conductive element 24 implemented as a conductive insert 194 including a body extending between proximal and distal ends 194A, 194B. The conductive insert 194 includes a first portion 196 for attaching to the distal plug 30 of the catheter tube 12 (see, e.g., FIG. 12B) and a second portion 198 that extends into the lumen of the catheter tube. The first portion 196 includes a single barb 202 for ensuring adequate engagement with the distal plug 30 of the catheter tube 12. This barb 202 is included to foreclose the possibility of the conductive insert 194 undesirably separating from engagement with the catheter tube 12. The barb 202 thus serves as an example of an engagement feature for attachment with the distal plug 30 of the catheter tube 12.

FIG. 18B shows that in another embodiment the first portion 196 can include multiple barbs 202 to enhance engagement of the conductive insert 194 with the distal plug 30 of the catheter tube 12. FIG. 18C shows that in one embodiment the conductive insert 194 can include threads 204 disposed along all or a portion of its body to enhance distal plug engagement.

FIG. 18D shows the conductive insert 194 according to one embodiment, wherein the body of the conductive insert defines a hollow core 206. The hollow core 206 enables the material from which the distal plug 30 is formed to flow into the hollow core during formation of the distal plug, thus enhancing engagement with the conductive insert 194. FIG. 18E shows that one or more side holes 208 can be defined through the body of the conductive insert 194 to further enhance distal plug engagement. And FIG. 18F shows that in one embodiment the conductive insert 194 can included a solid core, with holes 208 defined therein to enhance distal plug engagement. These and other variations for the conductive insert are therefore contemplated.

Figure 19:
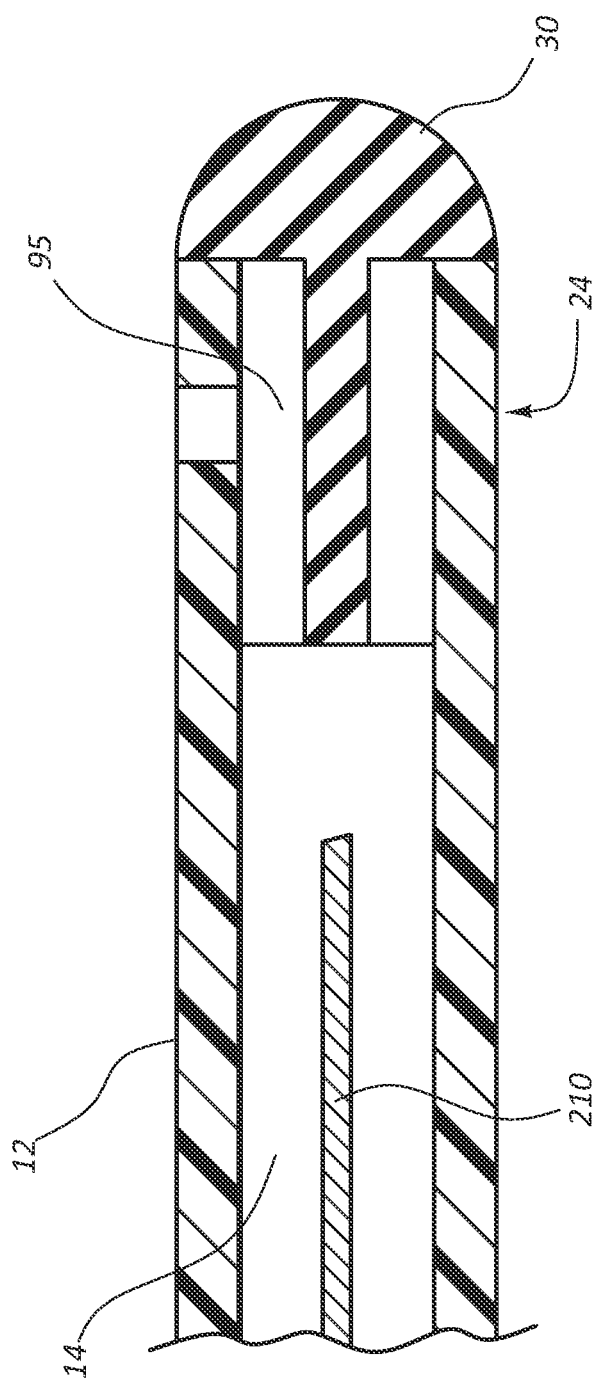
FIG. 19 is a cross-sectional view of a conductive pathway of a catheter tube according to one embodiment.

FIG. 19 depicts the conductive element 24 to provide an electrically conductive pathway in a closed-ended catheter tube according to another embodiment, wherein the conductive element includes the internal sleeve 95, similar to that shown in FIGS. 10A and 10B, disposed in the lumen 14 in a distal portion of the catheter tube 12. As shown, the silicone material from which the distal plug 30 is made fills the hollow core 95A of the internal sleeve 95 so as to enhance engagement between the distal plug and the internal sleeve. A stylet 210 is also shown in the lumen 14 proximate the internal sleeve 95. The stylet 210 can be used in one embodiment to help convey the electrical signal received by the internal sleeve via the hole 92 proximally up the catheter tube 12 and externally to a ECG monitoring device or other apparatus.

Figure 20:
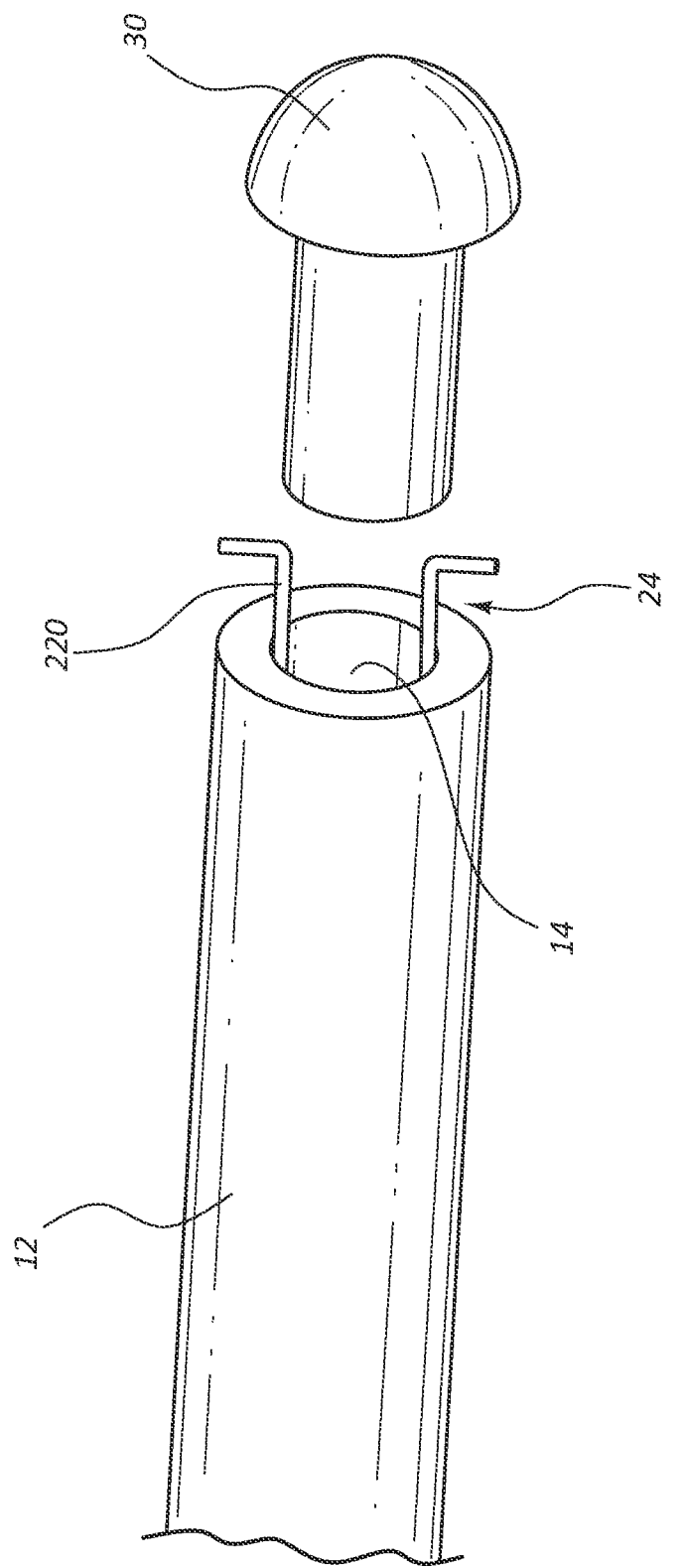
FIG. 20 is an exploded perspective view of a conductive pathway of a catheter tube according to one embodiment.

FIGS. 20 and 21 depict views of the conductive element 24 to provide an electrically conductive pathway in a closed-ended catheter tube according to one embodiment. In particular, FIG. 20 shows the conductive element 24 as including an elongate wire structure 220 that is interposed between the distal end of the catheter tube 12 and the distal plug 30 so as to provide a conductive pathway. FIG. 21 shows that the wire structure 220 includes a U-shaped body 222 that include two extensions 224. The wire structure 220 is attached to the catheter such that the U-shaped portion is disposed in the catheter tube lumen 14 and the two extensions 224 extend radially outward so as to be in contact with blood or other liquid in which the catheter tube 12 is disposed when inserted within the vessel of a patient. In this way, electrical signals present in the patient blood can be conveyed via the extensions 224 and body 222 of the wire structure 220 to saline or other fluid disposed in the catheter tube lumen 14. Note that the extensions 224 in the present embodiment are sized so as to terminate flush with the outer surface of the catheter tube, though this and other dimensions of the wire structure can vary. Also, though having here a round cross-sectional shape, the body 222 and extensions 224 of the wire structure 220 can define other cross-sectional shapes, including square, rectangular, substantially planar, triangular, etc. Also, different sections of the wire structure can define varying cross-sectional shapes. The wire structure 220 includes a conductive material, including titanium, nickel-titanium alloy, carbon fiber, stainless steel, and other metals and metal alloys.

Figure 22A:
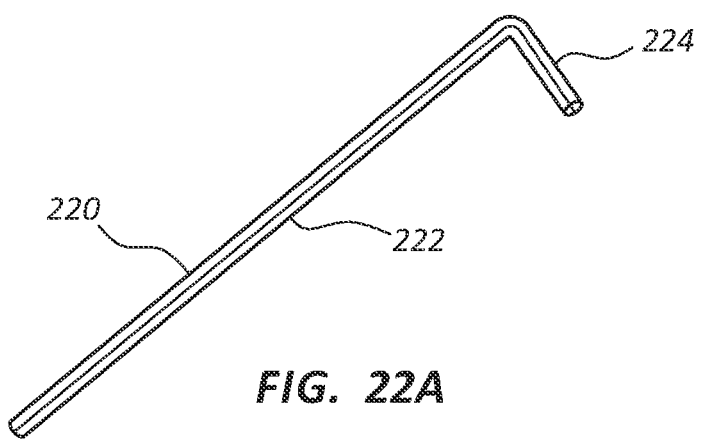
FIGS. 22A-22C are various views of conductive elements according to various embodiments.
Figure 22B:
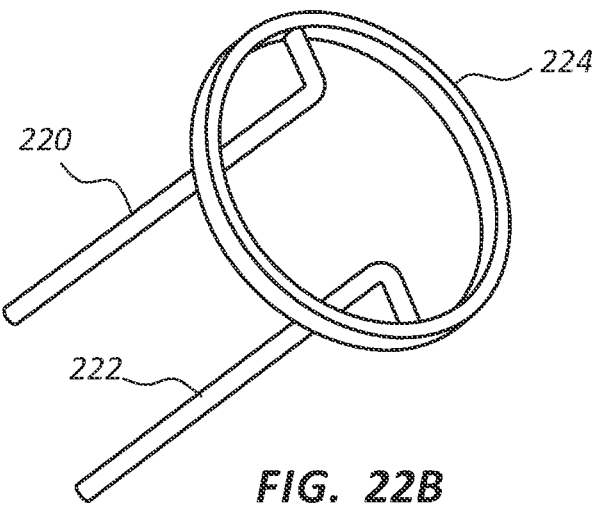
Figure 22C:
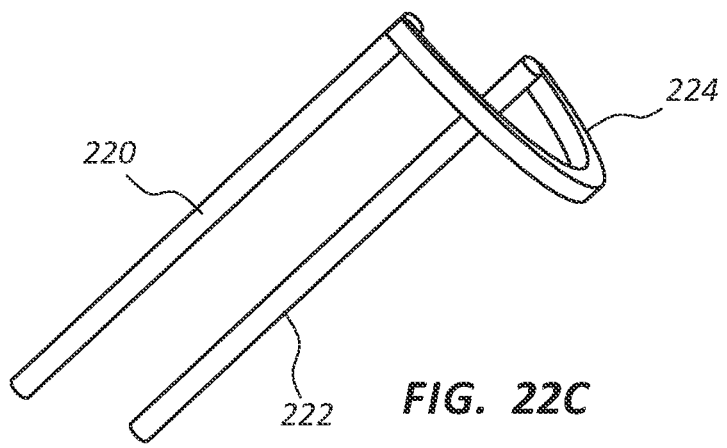

FIGS. 22A-22C give other non-limiting examples of possible configurations of the wire structure 220 including, in FIG. 22A, a wire structure including a linear body 222 with the extension 224 disposed at a substantially right angle thereto. In FIG. 22B, the wire structure 220 includes a body 222 defined by two parallel wires attached to a circular extension 224. In FIG. 22C, two parallel wires define the body 222 of the wire structure 220, with a semi-circular extension 224. These are other wire structure configurations are therefore contemplated.

Figure 23A:
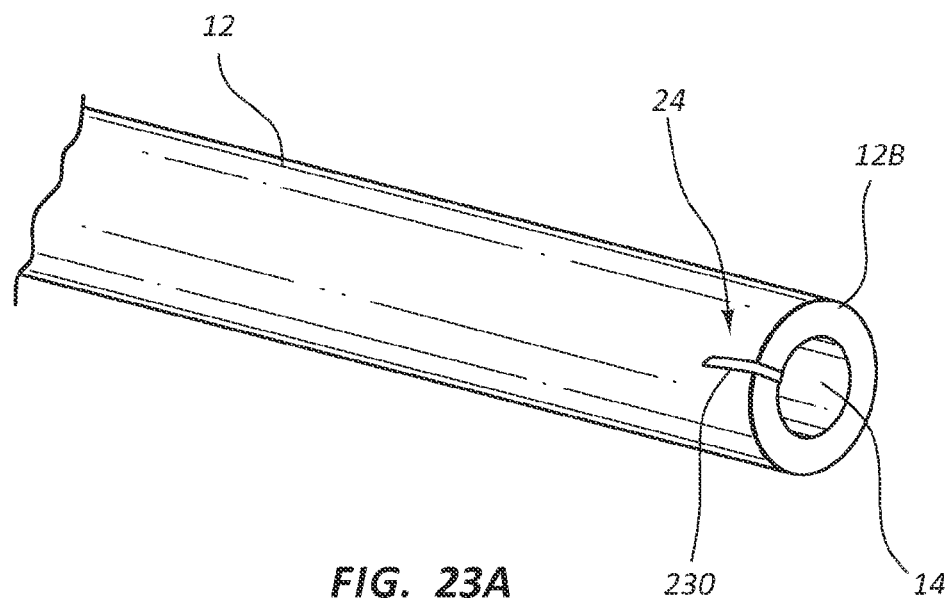
FIGS. 23A and 23B are various views of a conductive element according to one embodiment.
Figure 23B:
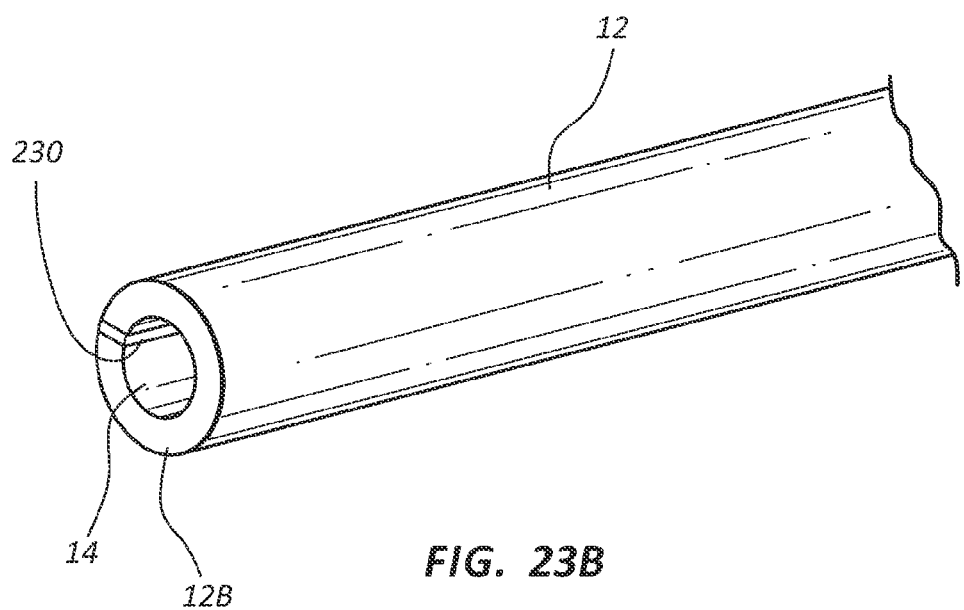

FIGS. 23A and 23B depict views of the conductive element 24 to provide an electrically conductive pathway in a closed-ended catheter tube according to one embodiment. As shown, the conductive element 24 includes a conductive pathway 230 that is disposed on the catheter tube 12 from a fluid-contacting point on the outer surface of the catheter tube 12 to a fluid-contacting point on an internal surface of the lumen 14. For instance, in the illustrated embodiment the conductive path 230 extends from a point just proximal to the distal end of the catheter tube 12 on the outer surface thereof, around the distal end of the catheter tube and to a point just proximal to the distal end on an interior surface of the lumen 14. The distal plug of the catheter tube 12 is omitted from the view in FIGS. 23A and 23B. In another embodiment, the conductive path 230 can extend proximally further up the catheter tube 12 on either or both of the external and internal surfaces thereof, including to the proximal end of the catheter assembly. A plurality of other conductive pathways can be employed, including those that are bored through the wall of the catheter tube 12.

In the present embodiment, the conductive pathway includes a conductive ink that is painted on the catheter tube surface. In other embodiments, however, the conductive ink can be disposed within a track, hole, raised surface, etc., defined in/on the catheter tube so as to provide a pathway for the transit of electrical signals from the patient blood within the vessel in which the catheter tube 12 is disposed to liquid saline or other fluid disposed within the catheter tube lumen 14. Examples of suitable conductive inks that can be employed include silver or carbon-containing inks, etc. In one embodiment, all or a portion of the catheter tube 12 can be treated so as to enhance the adhesion of the conductive ink to the catheter tube surface.

In yet another embodiment, the conductive pathway can include a stripe of conductive ink or other conductive pathway included in the catheter so as to extend between proximal and distal ends of the catheter (or some intermediary locations between the proximal and distal ends) so as to enable an electrical signal detected at or near the distal end to be conveyed along the length of the catheter to a monitoring apparatus outside the body of the patient. One or more portions of such a conductive ink stripe can be integrated into the wall of the catheter tube below the external surface thereof, in one embodiment.

In one embodiment, a portion of the catheter itself can define a conductive pathway. Indeed, in one embodiment the distal plug, such as the distal plug 30 shown in FIG. 19 for instance, can be formed so as to be sufficiently conductive, thus providing a conductive pathway between the exterior of the catheter tube 12 and the internal lumen 14 thereof. In one embodiment, the distal plug includes a mixture of a conductive ink and conductive silicone, though other suitable conductive materials can be utilized. Specifically, in one embodiment a mixture including 50 percent (by weight) MED 4843 conductive silicone elastomer (available from NuSil Technology LLC, 1050 Cindy Lane, Carpinteria, Calif. 93013) and 50 percent (by weight) 117-23 medical grade electrically conductive ink including silver (available from Creative Materials, Inc., 12 Willow Road, Ayer, Mass. 01432) is used to form the distal plug 30 of the catheter tube 12 so as to enable electrical signals to pass therethrough. Other conductive, medical grade materials can be used in other embodiments, including those that contain carbon black and silver, for instance.

In other embodiments other mixture concentrations are possible, including 45%/55% or 40%/60% concentrations by weight (conductive silicone to conductive ink). Note that other concentrations are also possible. Non-conductive silicone may also be used, in one embodiment, with a relatively greater concentration of conductive ink. The conductive ink discussed in connection with the present embodiment can be employed with other embodiments herein. In another embodiment, a portion of the catheter tube 12 proximal to the distal end can include an electrically conductive material, such as the conductive silicone/conductive ink mixture discussed above, so as to define an electrically conductive pathway therethrough.

In yet another embodiment, a technique can be employed whereby the catheter tube is continually infused with an electrically conductive solution, such as sterile saline, while monitoring for an electrical signal. The continual flushing opens the distal valve of the catheter tube, thus enabling electrical signals in the bloodstream of the patient to be conducted through the saline passing through the valve and up the saline column within the catheter tube lumen so as to be detected by external monitoring apparatus connected to the catheter assembly. The connector assembly 110 shown in FIG. 17 can be employed with the present technique, in one embodiment, such that the conductive wire 120 is operably connected with, and conveys signals present in the saline column of the catheter tube lumen to, the external monitoring apparatus.

Figure 24A:
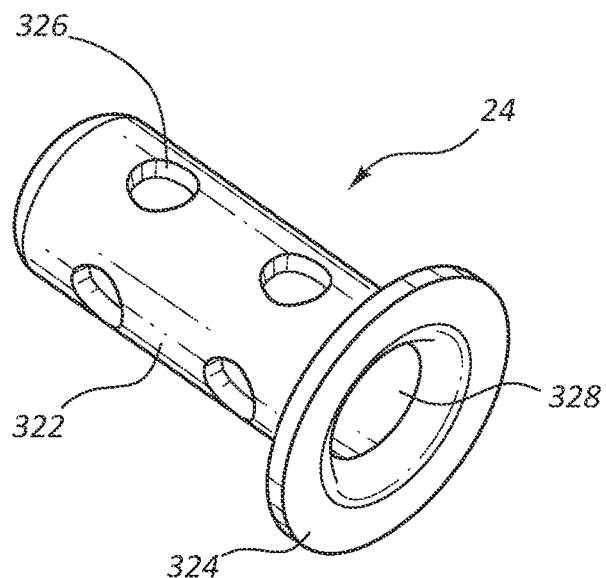
FIGS. 24A and 24B are various views of a conductive element according to one embodiment.

FIGS. 24A-28 depict views of the conductive element 24 to provide an electrically conductive pathway in a closed-ended catheter tube according to additional embodiments. FIGS. 24A and 24B show that the conductive element 24 includes in one embodiment a conductive insert defining a hollow body 322 with a plurality of 326 side holes defined therein. A central hole 328 is also defined by the body 322. An annular flange 324 is also included. FIG. 24B shows the manner in which the body 322 of the conductive insert is attached to the distal portion of the catheter tube 12, wherein the flange 324 is interposed between the distal end of the catheter tube and the distal plug 30 such that a portion of the flange is disposed on an external portion of the catheter tube. The distal plug is formed about and within the body 322 of the conductive insert via the side holes 326 and central hole 328 so as to secure the body in place. So disposed, the body 322 defines a conductive pathway from the exterior of the catheter tube 12 to the internal lumen 14.

Figure 24B:
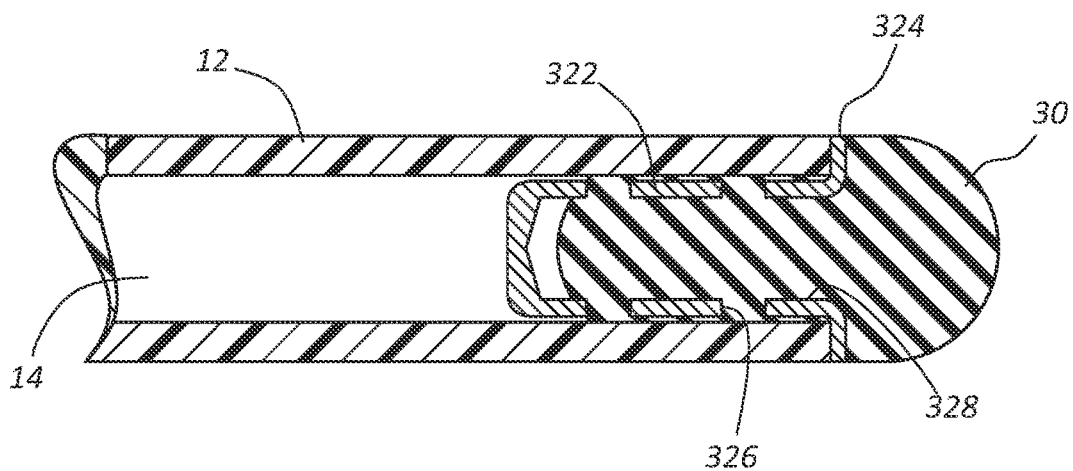
Figure 25:
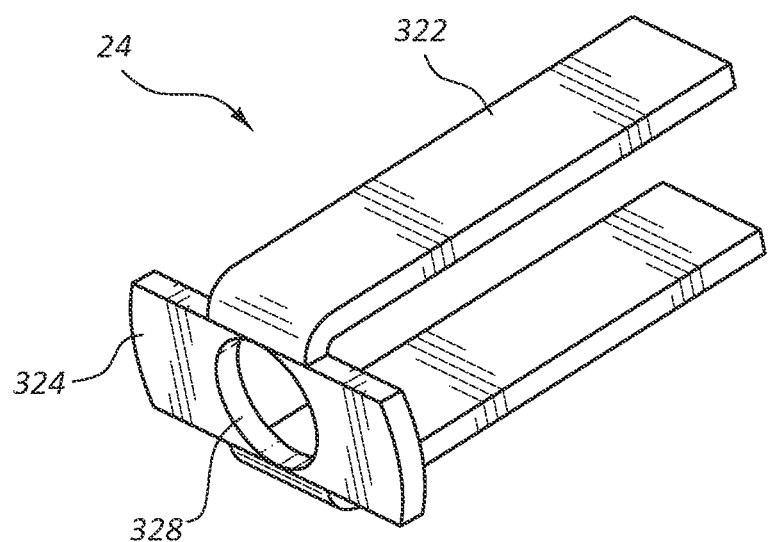
FIG. 25 is a perspective view of a conductive element according to one embodiment.
Figure 26:
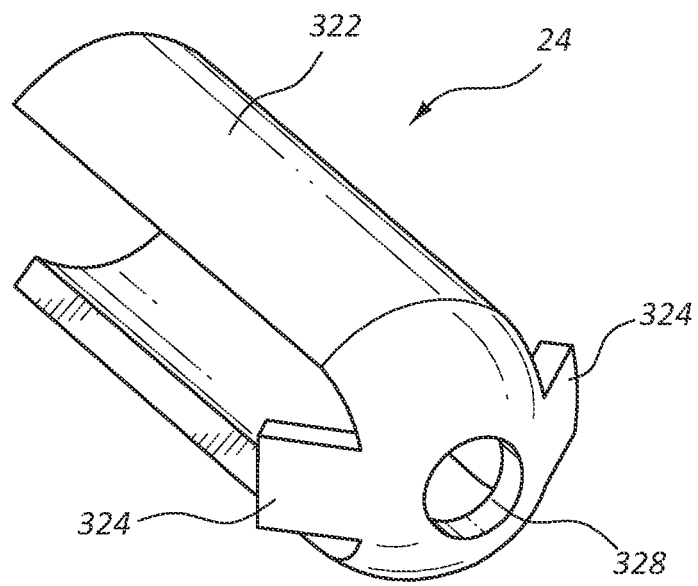
FIG. 26 is a perspective view of a conductive element according to one embodiment.
Figure 27:
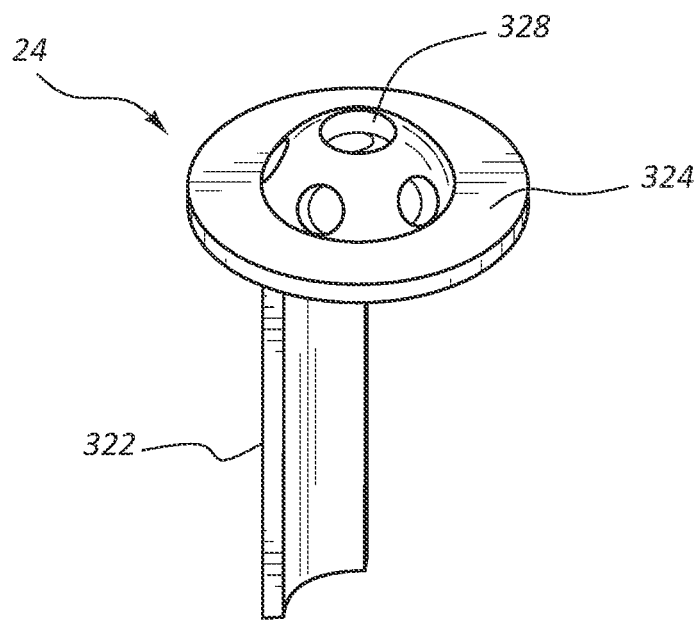
FIG. 27 is a perspective view of a conductive element according to one embodiment.
Figure 28:
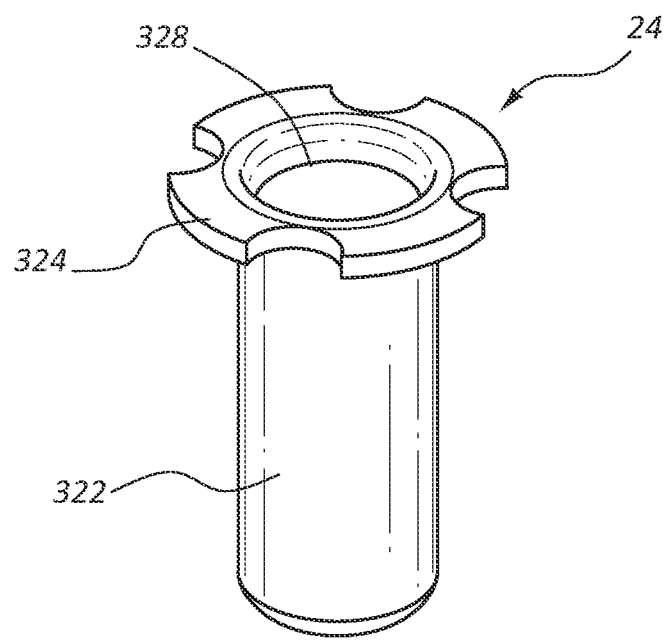
FIG. 28 is a perspective view of a conductive element according to one embodiment.

In addition to that shown in FIGS. 24A and 24B, the conductive insert can include other designs. For instance, FIG. 25 shows the body 322 as including two elongate, parallel arms, with the bar-like flange 324 defining the central hole 328. In FIG. 26, the body 322 defines two elongate, arcuate arms and the flange 324 defining the hole 328 and including two angled extensions. In FIG. 27, the body 322 includes a single elongate, arcuate arm, the flange 324 includes a saucer-like disk with the central hole 328 defined therein. And in FIG. 28, the body 322 defines a hollow cylinder, while the flange 324 defines an annular, notched shape surrounding the central hole 328. In each of the embodiments of FIGS. 24A-28, the flange 324 provides a pathway through the wall of the catheter tube 12 to the body 322 to enable electrical signals to pass from the exterior of the catheter tube to the lumen 14, as desired. In addition to the afore-mentioned, other conductive insert shapes can be employed.

Figure 29:
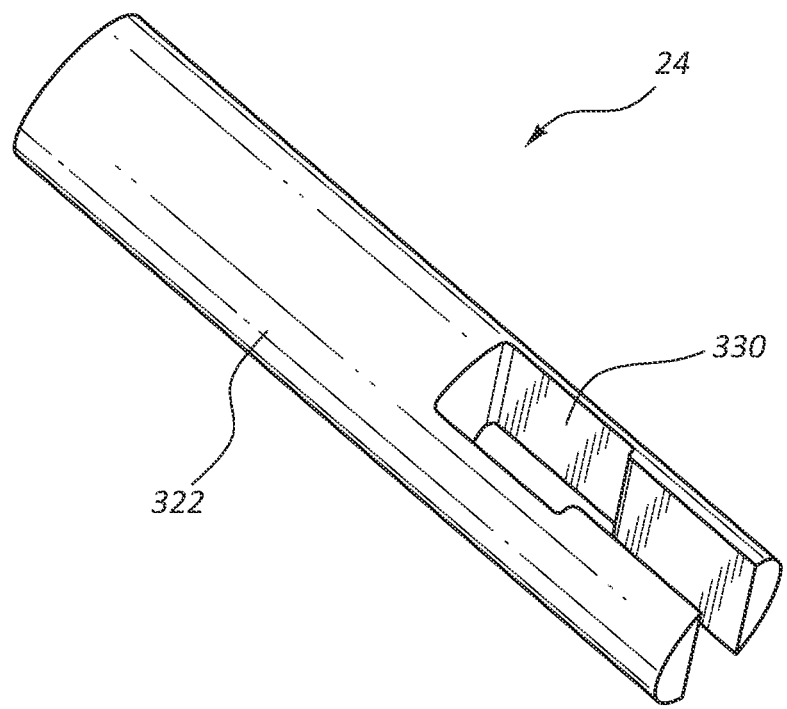
FIG. 29 is a perspective view of a conductive element according to one embodiment.

FIG. 29 shows the conductive element 24 according to one embodiment, including a conductive insert for disposal within the lumen 14 of the catheter tube 12. The conductive insert is defined by the body 322, which in turn defines an open-ended slot 330. The conductive insert body 322 is disposed within the catheter tube lumen 14 in one embodiment such that a side hole defined in the catheter tube 12 is disposed adjacent a portion of the conductive insert body so as to enable electrical signals to pass from outside of the catheter tube to within the lumen 14 via the body, all without the transfer of fluid through the hole, given the relatively tight fit between the conductive insert body 322 and the side hole.

Figure 30:
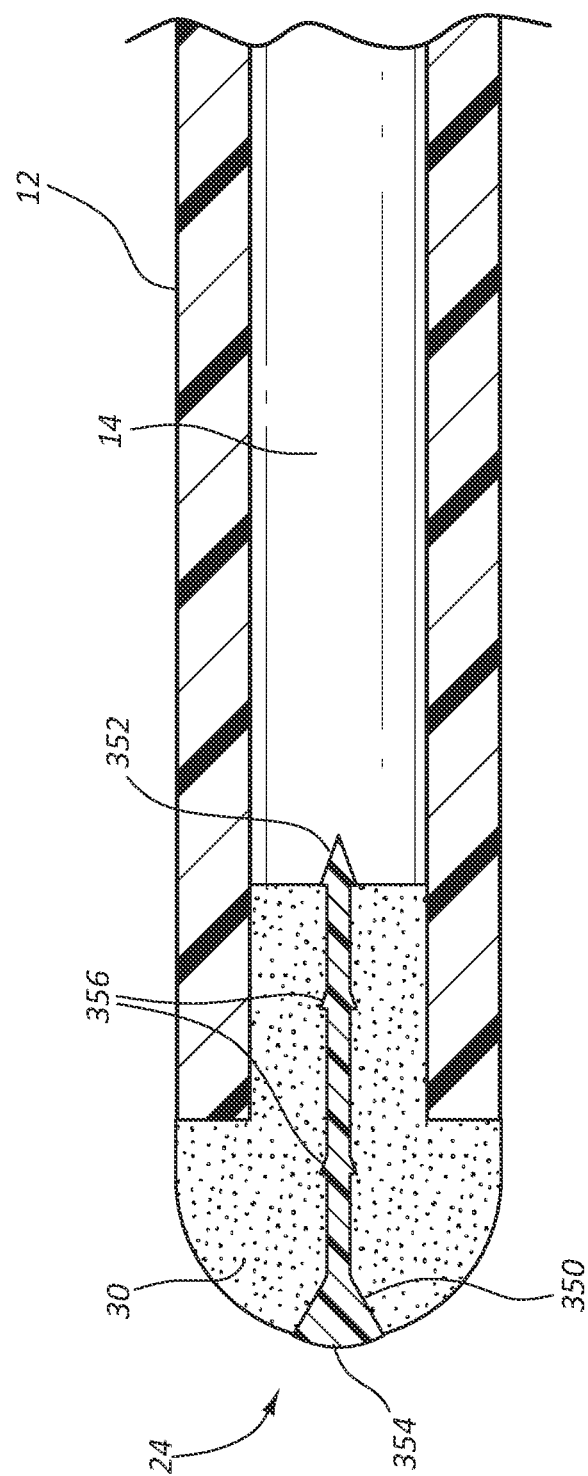
FIG. 30 is a cross-sectional side view of a conductive element according to one embodiment.

FIG. 30 depict views of the conductive element 24 to provide an electrically conductive pathway in a closed-ended catheter tube according to one additional embodiment, wherein the conductive element includes a conductive spike 350 that defines a spiked proximal end 352, a rounded distal end 354, and intermediately-placed barbs 356. The spiked proximal end 352 and barbs 356 assist with maintaining engagement with the distal plug 30, while the rounded distal end 354 matches the rounded shape of the distal plug. As shown, the spike 350 forms a conductive pathway for electrical signals to be conveyed from the exterior of the catheter tube 12 to the internal lumen 14, as desired. The particular, size, length, shape, and other features of the conductive spike can be modified from what is shown and described herein.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

The invention claimed is:

1. A catheter assembly for placement in a body of a patient, comprising:
   an elongate catheter tube including a closed distal end, the catheter tube defining at least one lumen;
   a valve defined in the catheter tube configured to selectively enable fluids to pass therethrough; and
   a conductive element that provides an electrically conductive pathway between the at least one lumen and an exterior portion of the catheter tube, the conductive element including:
      an electrically conductive wire structure, including a first portion disposed within the at least one lumen of the catheter tube and a second portion extending to at least an outer surface of the catheter tube so as to enable the second portion to be in contact with fluids in a vessel of the body of the patient in which the catheter tube is disposed.

2. The catheter assembly as defined in claim 1, wherein the first portion is substantially U-shaped.

3. The catheter assembly as defined in claim 1, wherein the second portion is disposed at substantially a right angle with respect to the first portion.

4. The catheter assembly as defined in claim 1, wherein the first portion is substantially linear.

5. The catheter assembly as defined in claim 1, wherein the second portion is interposed between a distal end of the catheter tube and a distal plug disposed in the distal end of the catheter tube.

6. The catheter assembly as defined in claim 1, wherein the second portion is circular.

7. The catheter assembly as defined in claim 1, wherein the second portion is semi-circular.

* * * * *